United States Patent [19]

Kinlen et al.

[11] Patent Number: 5,110,441
[45] Date of Patent: May 5, 1992

[54] SOLID STATE PH SENSOR

[75] Inventors: Patrick J. Kinlen, Fenton; Hilliard L. Williams, Chesterfield, both of Mo.

[73] Assignee: Monsanto Company, St. Louis, Mo.

[21] Appl. No.: 450,783

[22] Filed: Dec. 14, 1989

[51] Int. Cl.⁵ .......................................... G01N 27/30
[52] U.S. Cl. .................................. 204/418; 204/433; 204/435
[58] Field of Search ............. 204/433, 435, 418, 153.21

[56] References Cited

U.S. PATENT DOCUMENTS

| | | | |
|---|---|---|---|
| 3,726,777 | 4/1973 | Macur | 204/433 X |
| 4,507,194 | 3/1985 | Shimomura et al. | 204/435 |
| 4,519,973 | 5/1985 | Cahalan et al. | 204/435 X |
| 4,734,184 | 3/1988 | Burleigh et al. | 204/409 |
| 4,797,192 | 1/1989 | Takiguchi | 204/412 |
| 4,818,361 | 4/1989 | Burgess et al. | 204/406 |
| 4,818,365 | 4/1989 | Kinlen et al. | 204/433 |
| 4,908,117 | 3/1990 | Kinlen et al. | 204/415 |

FOREIGN PATENT DOCUMENTS 1-36060 5/1989 Japan.

Primary Examiner—John Niebling
Assistant Examiner—William T. Leader

[57] ABSTRACT

A solid state pH sensor having an indicator electrode of metal/metal oxide and a reference electrode of metal/metal salt applied to electrically conductive conductors, such as electrically conductive cermet conductors and electrically conductive metal pins, imbedded in an electrically non-conductive substrate, such as electrically non-conductive ceramic substrates including S-glass substrates. The sensing portion of the sensor preferably has a coating of an annealed perfluorocarbon copolymer. Alternatively, the indicator or reference electrodes may be formed on separate electrically non-conductive substrates with each having an electrically conductive conductor imbedded therein. These indicator or reference electrodes may be utilized with each other or with prior art indicator or reference electrodes.

8 Claims, 14 Drawing Sheets

SOLID STATE PH SENSOR

FIELD OF THE INVENTION

This invention relates to a solid state pH sensor having an indicator electrode of metal/metal oxide and a reference electrode of metal/metal salt applied to electrically conductive conductors, such as electrically conductive cermet conductors and electrically conductive metal pins, imbedded in an electrically non-conductive substrate, such as electrically non-conductive ceramic substrates including S-glass substrates. The sensing portion of the sensor preferably has a coating of an annealed perfluorocarbon copolymer.

BACKGROUND OF THE INVENTION

Electrolytic sensors for detecting and measuring the pH of a liquid system (a measurement of the hydrogen ion activity) are well known. Generally such pH sensors include a glass membrane electrode and a reference electrode. The glass electrodes tend to be quite fragile, and are therefore not generally suitable for applications where the electrodes are subjected to a considerable amount of movement, jostling or shock, or high temperatures or pressures.

Junction-type metal/metal oxide solid state pH electrodes have been proposed for sensing the pH of solutions and other fluids. These electrodes have the sought after advantages of stability in aqueous solutions over a wide range of temperatures and pressures, low impedance and fast response to pH changes. Fog et al., "Electronic Semiconducting Oxides as pH Sensors", *Sensors and Actuators*, 5 (1984) 137–146, discuss the limitations of such pH sensors. Oxidizing and reducing agents, such as ferricyanide, ferrocyanide and hydrogen peroxide were found to interfere with pH measurement. In addition, pH sensors which utilize the junction-type electrodes discussed therein, retain the limitations of the glass electrodes discussed above, when coupled with a conventional reference electrode.

Various improvements have been made on the junction-type electrode to make it more rugged and compact.

U.S. Pat. No. 3,905,889 discloses a pH sensor in which the reference and indicator electrodes are surrounded by an electrolyte and encased in a hydrogen ion and carbon dioxide permeable diffusion barrier, such as poly(siloxane)-poly(bisphenol-A) polycarbonate block copolymer. The effective pH range for this probe is very limited, from 5.6 to 7.1.

U.S. Pat. No. 4,536,274 discloses a transcutaneous blood carbon dioxide sensor which utilizes a junction-type electrode of palladium/palladium oxide and a silver/silver halide electrode applied to an electrically nonconductive substrate, partially coated with an insulated dielectric and the remainder thereof optionally coated with any of a number of polymeric membrane materials, including perfluorocarbon copolymers. This pH sensor is limited to measuring a narrow pH range of from 6.49 to 8.50, and is characterized by slow responsiveness and poor reproducibility.

Though these electrodes may be more rugged than the glass membrane electrodes, inherent mechanical sealing problems exist with these electrodes, including glass membrane electrodes, particularly when utilized for on-line pH monitoring in high pressure and/or high temperature processes. For example, compression seals in such applications generally utilize sealing polymers which flow when heated causing the seal to break down and leak upon temperature cycling. To complicate matters, those sealing polymers which do not flow upon heating generally take-up water, i.e., hydrate (0.06% w or more water), leading to a low resistance leakage path between electrodes. This leakage path essentially short circuits the electrodes resulting in an erroneous pH reading.

Thus, there exists a need to make a pH sensor and electrodes therefor which are rugged, compact and seal-less.

SUMMARY OF THE INVENTION

Accordingly, a feature of the present invention is to provide a pH sensor and electrodes therefor which are rugged and compact plus adaptable for use with or without seals.

More particularly, there is provided a solid state pH sensor for pH sensing equipment, the pH sensor comprising:
  (a) an indicator electrode, the indicator electrode comprising
    (1) a first electrically conductive conductor imbedded in a first electrically non-conductive substrate, the first electrically conductive conductor having a first electrically conductive conductor exposed portion,
    (2) a metal/metal oxide coating on the first electrically conductive conductor exposed portion, such that the metal/metal oxide coating entirely covers the first electrically conductive conductor exposed portion, and
    (3) an indicator contact zone electrically connected to the first electrically conductive conductor, wherein the indicator contact zone is utilized in making electrical contact between the first electrically conductive conductor and the pH sensing equipment, and
  (b) a reference electrode, the reference electrode comprising
    (1) a second electrically conductive conductor imbedded in a second electrically non-conductive substrate, the second electrically conductive conductor having a second electrically conductive conductor exposed portion,
    (2) a metal/metal salt coating on the second electrically conductive conductor exposed portion, such that the metal/metal salt coating entirely covers the second electrically conductive conductor exposed portion, and
    (3) a reference contact zone electrically connected to the second electrically conductive conductor, wherein the reference contact zone is utilized in making electrical contact between the second electrically conductive conductor and the pH sensing equipment,
  (c) wherein the indicator and reference electrodes are electrically insulated from each other and
  (d) wherein the reference electrode is in contact with a reference electrolyte source.

The electrically conductive conductors may be of many suitable electrically conductive material, for example, electrically conductive cermets, electrically conductive metals, and silicon which has been doped to render same electrically conductive.

The electrically non-conductive substrate may be of any suitable electrically non-conductive material, for example, electrically non-conductive ceramics, silicon, and synthetic polymers.

Preferably, the foregoing pH sensor further comprises an immobilized electrolyte coating on the metal/metal salt coating as the reference electrolyte source, such that the immobilized electrolyte coating entirely covers the metal/metal salt coating.

More preferably and in addition to the foregoing, the pH sensor further comprises a first perfluorocarbon copolymer coating on the metal/metal oxide coating, such that the first perfluorocarbon copolymer coating entirely covers the metal/metal oxide coating, and a second perfluorocarbon copolymer coating on the immobilized electrolyte coating, such that the second perfluorocarbon copolymer coating entirely covers the immobilized electrolyte coating.

A particularly preferred embodiment of the present invention is one in which the perfluorocarbon copolymer of the first and second perfluorocarbon copolymer coatings is annealed. A change in the molecular configuration of the perfluorocarbon copolymer occurs during the annealing process which improves the copolymer's rejection of interfering ions.

The perfluorocarbon copolymer utilized herein is preferably an acid or salt derivation of a base copolymer comprising at least two monomers wherein one monomer is selected from a group consisting of a vinyl fluoride, hexafluorpropylene, chlorotrifluoroethylene, perfluoro-(alkyl vinyl ether) and tetrafluoroethylene, and the second monomer is selected from the group of monomers containing an $-SO_2F$ or $-COF$ group. The base copolymer is then converted to an acid derivative thereof or a salt of this acid derivative. For example, the base copolymer may be converted to the acid or salt derivative thereof by hydrolyzing the base copolymer.

This indicator and reference electrodes of the present invention may be utilized with each other or individually in conjunction with its conventional or prior art reference or indicator electrode counterpart, respectively.

In another embodiment, the indicator and reference electrodes may have a common, single electrically non-conductive substrate wherein a first portion of the single electrically non-conductive substrate takes the place of the first electrically non-conductive substrate and a second portion of the single electrically non-conductive substrate takes the place of the second electrically non-conductive substrate. In such an embodiment, the first and second annealed perfluorocarbon copolymer coatings may be combined into a single annealed perfluorocarbon copolymer coating.

As earlier noted, the individual indicator or reference electrode of the present invention may be utilized in conjunction with its conventional or prior art reference or indicator electrode counterpart, respectively. Thus, there is also provided in a pH sensor for pH sensing equipment, an electrode, the electrode comprising (a) an electrically conductive conductor imbedded in an electrically non-conductive substrate, the electrically conductive conductor having an exposed portion;

(b) an electrode-typing coating on the exposed portion, such that the electrode-typing coating entirely covers the exposed portion, the electrode-typing coating selected from the group consisting of a metal/metal oxide coating for indicator electrodes, an electrically conductive metal oxide coating for indicator electrodes (e.g., $PtO_2$, $IrO_2$, $RuO_2$, $PbO_2$, $Ta_2O_5$ and $TiO_2$) and a metal/metal salt coating for reference electrodes (e.g., Ag/AgCl); and (c) a contact zone electrically connected to the electrically conductive conductor, wherein the contact zone is utilized in making electrical contact between the electrically conductive conductor and the pH sensing equipment.

Preferably, when the metal/metal salt coating is selected as the electrode-typing coating, the electrode (now a reference electrode) further comprises an immobilized electrolyte coating on the metal/metal salt coating as the reference electrolyte source therefor, such that the imobilized electrolyte coating entirely covers the metal/metal salt coating.

The electrode, indicator or reference electrode, preferably also comprises an annealed perfluorocarbon copolymer coating on the electrode-typing coating, or the immobilized electrolyte coating (if present), such that the annealed perfluorocarbon copolymer coating entriely covers the electrode-typing coating, or the immobilized electrolyte coating.

There is further provided a process for preparing a solid state pH sensor for pH sensing equipment, the process comprising the steps of:

(1) cleaning and polishing the surface of an electrically non-conductive substrate having at least two electrically conductive conductors imbedded therein wherein the conductors are electrically insulated from each other and each of the conductors has at least one exposed portion. (2) applying a metal/metal oxide coating of the exposed portion of the first electrically conductive conductor, such that the metal/metal oxide coating entirely covers the exposed portion of the first electrically conductive conductor, (3) applying a metal/metal salt coating to the exposed portion of the second electrically conductive conductor such that the metal/metal salt coating does not contact the metal/metal oxide coating of the first electrically conductive conductor and such that the metal/metal salt coating entirely covers the exposed portion of the second electrically conductive conductor, (4) applying an immobilized electrolyte to the metal/metal salt coating of the second electrically conductive conductor, such that the immobilized electrolyte entirely covers the metal/metal salt coating, (5) applying a perfluorocarbon copolymer coating to completely cover the metal/metal oxide and the immobilized electrolyte of the first and second electrically conductive conductors, respectively, (6) annealing the perfluorocarbon copolymer coating so as to change the morphology of the copolymer to that which improves the rejection of interferences by the copolymer, and (7) hydrating the immobilized electrolyte coating and the annealed perfluorocarbon copolymer coating.

Accordingly, these and other features and advantages of the present inventionwill become apparent from the following detailed description, wherein reference is made to the figures in the accompanying drawings.

IN THE DRAWINGS

Figure 6:
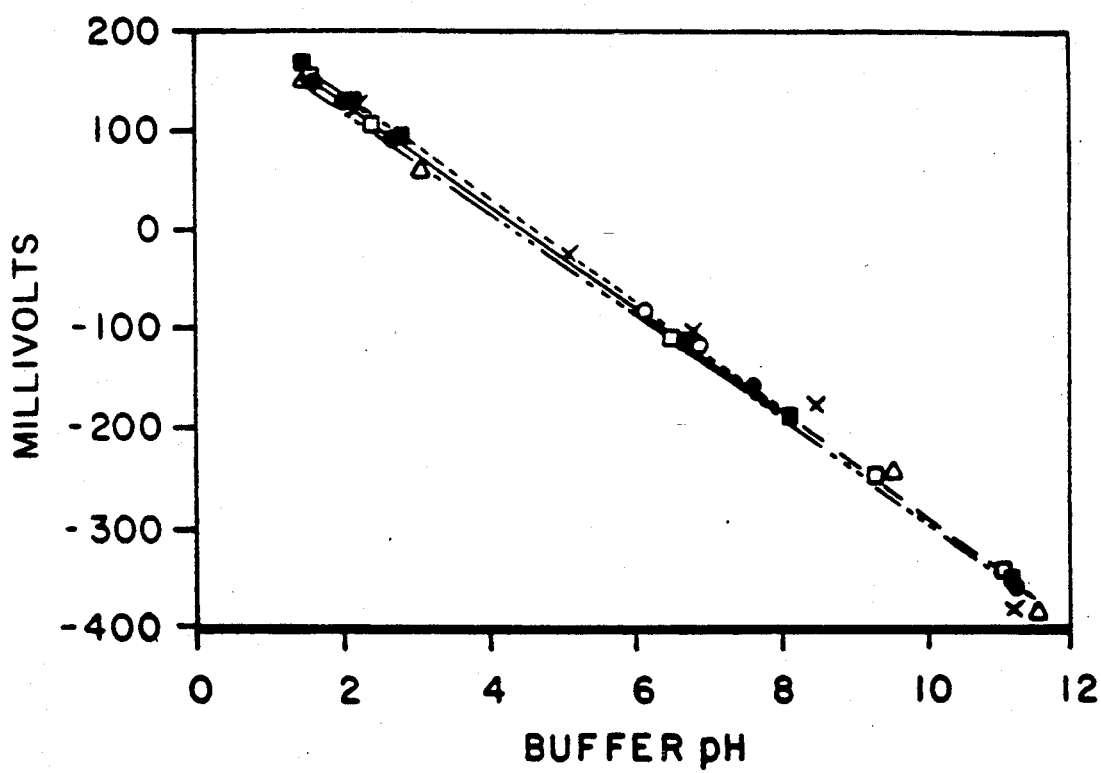

FIG. 6. 70-day repeatability plot of the standardization curve for $IrO_2$/Cermet Indicator Electrode.

Figure 7:
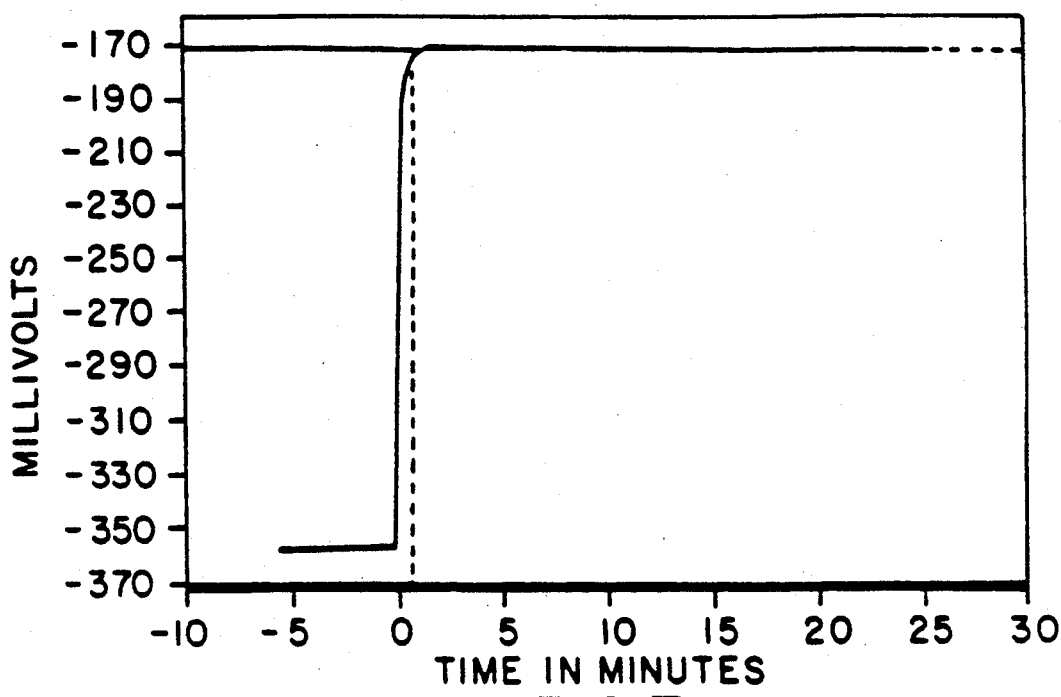

FIG. 7. pH response curve (potential vs. time after a step change in pH) for $IrO_2$/Cermet Indicator Electrode.

Figure 8:
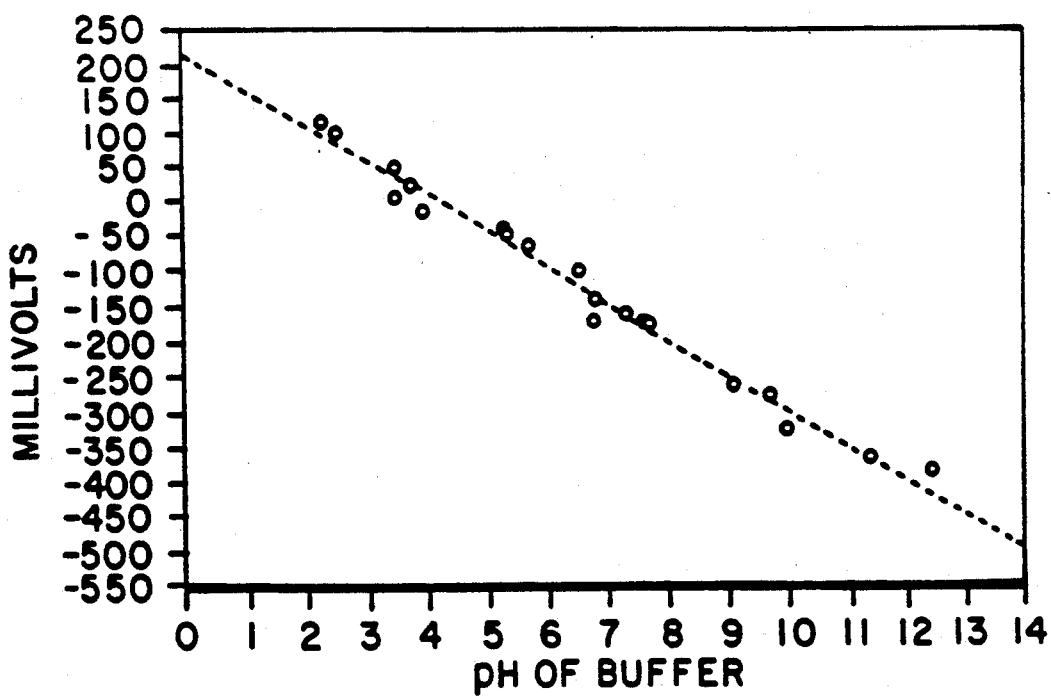

FIG. 8. Nernst plot (pH vs. potential) for $IrO_2$/Cermet Indicator Electrode.

Figure 9:
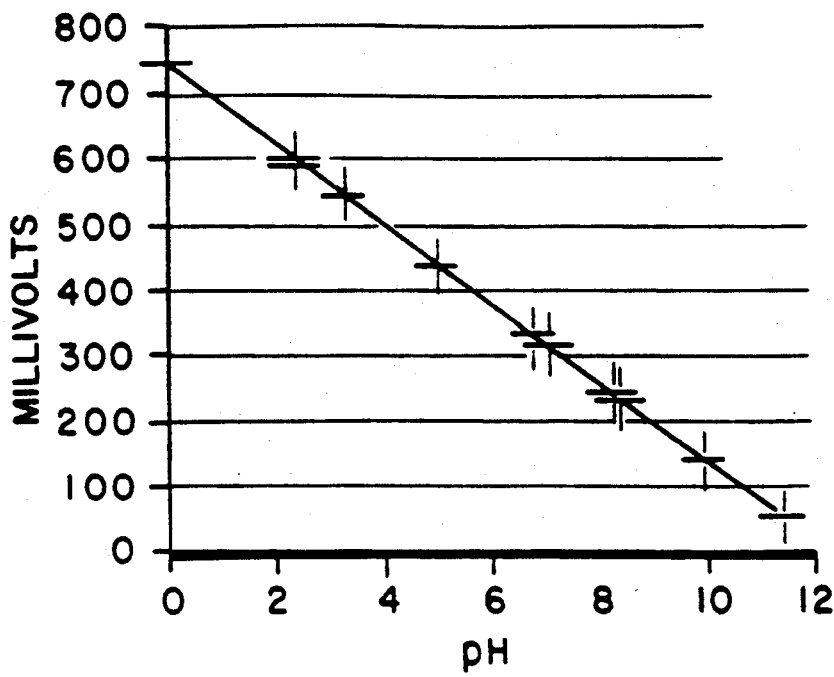

FIG. 9. Nernst plot for $IrO_2$/polished Au/Cermet Indicator Electrode.

Figure 10:
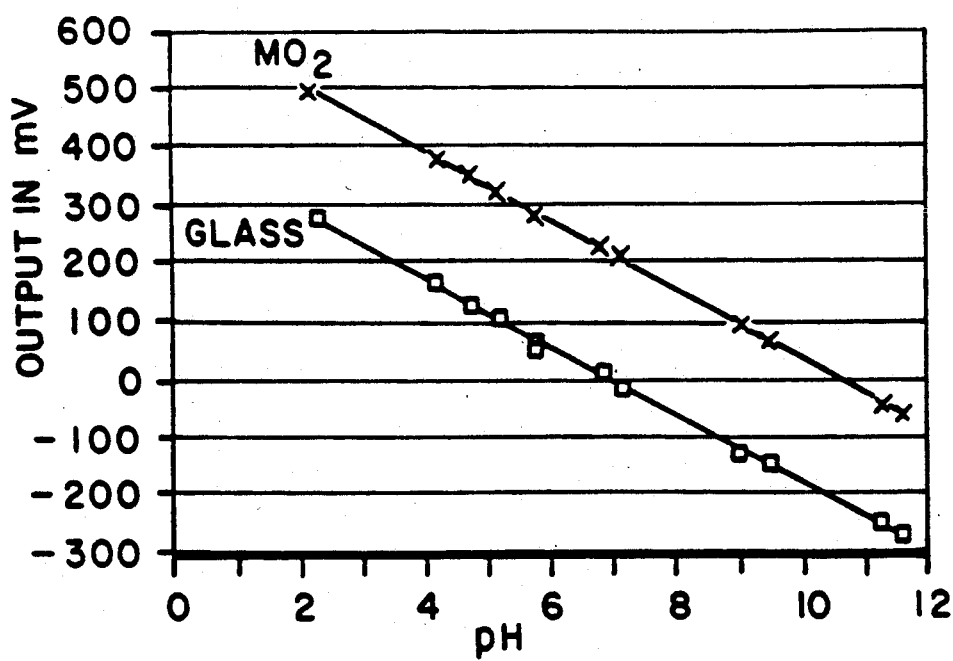

FIG. 10. Nernst plot for $IrO_2$/Ti/Au/Cermet Indicator Electrode.

Figure 11:
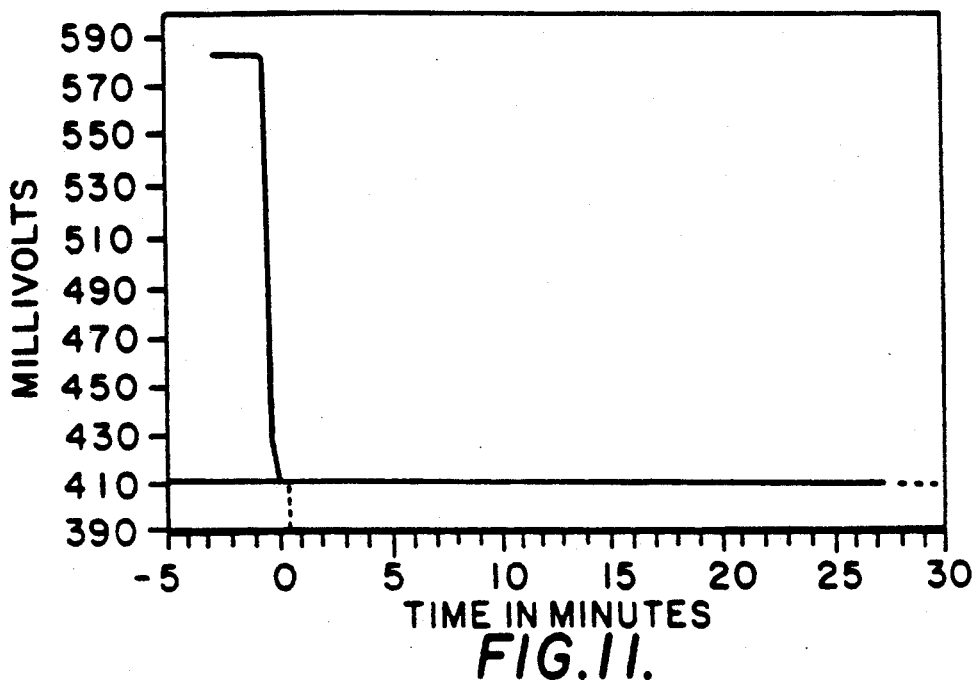

FIG. 11 pH response curve for $IrO_2$/Ir/Ti/Au/Ti/Cermet in Ceramic Indicator Electrode for pH 2.5 to 5.18.

Figure 12:
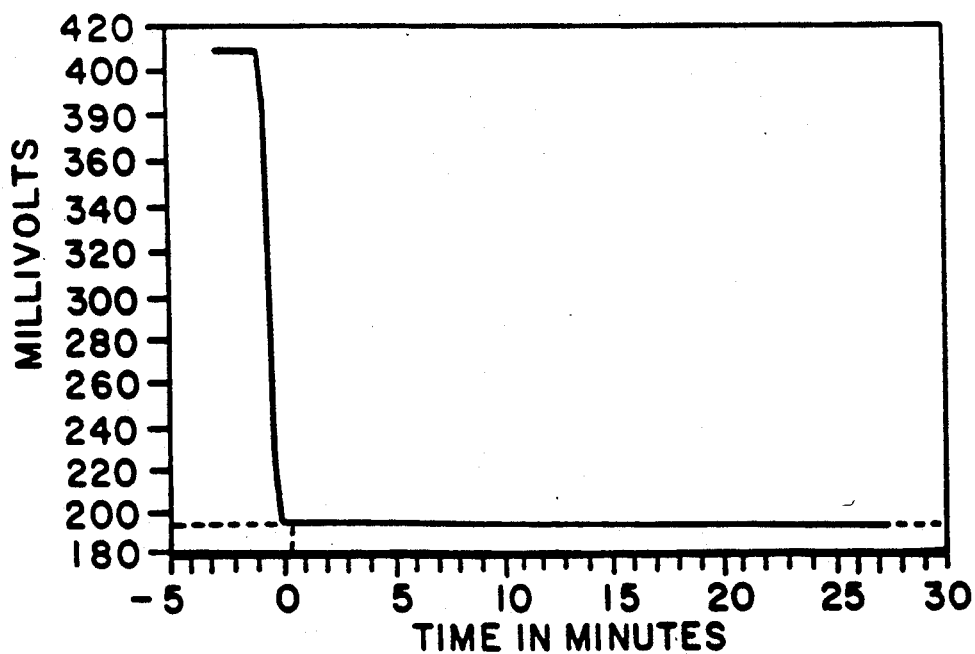

FIG. 12. pH response curve for $IrO_2$/Ir/Ti/Au/Ti/Cermet in Ceramic Indicator Electrode for pH 5.44 to 8.78.

Figure 13:
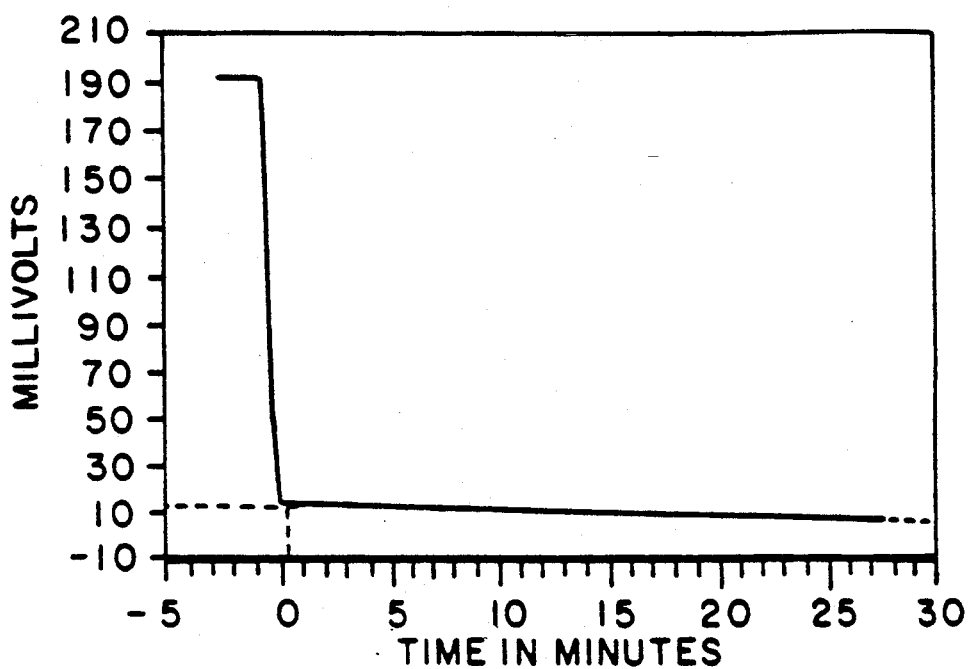

FIG. 13. pH response curve for $IrO_2$/Ir/Ti/Au/Ti/Cermet in Ceramic Indicator Electrode for pH 8.95 to 11.72.

Figure 14:
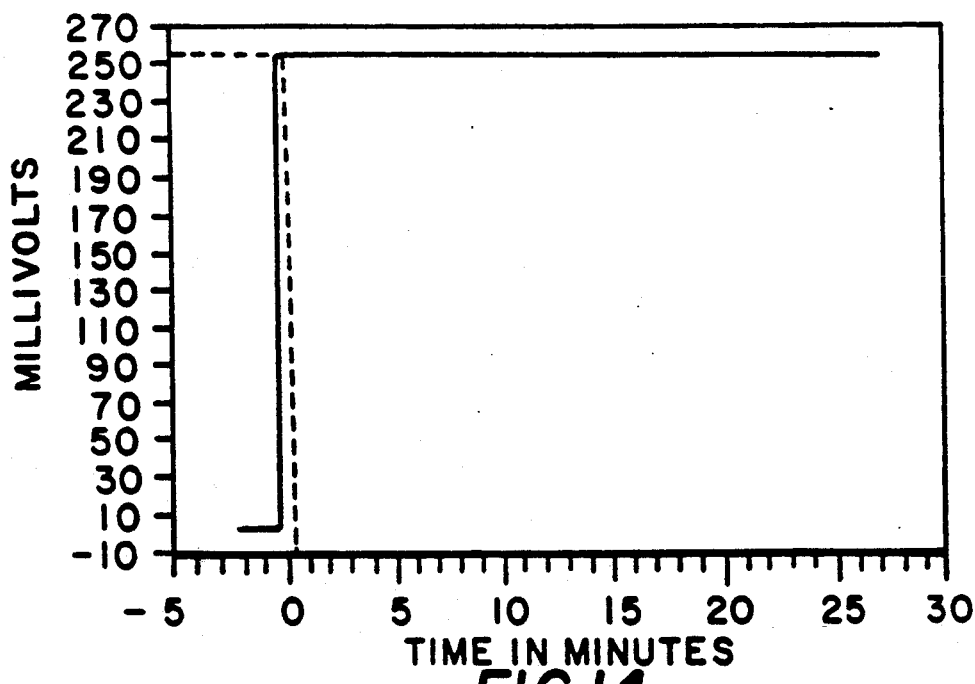

FIG. 14. A back titration pH response curve for $IrO_2$/Ir/Ti/Au/Ti/Cermet in Ceramic Indicator Electrode pH 11.53 to 7.56.

Figure 15:
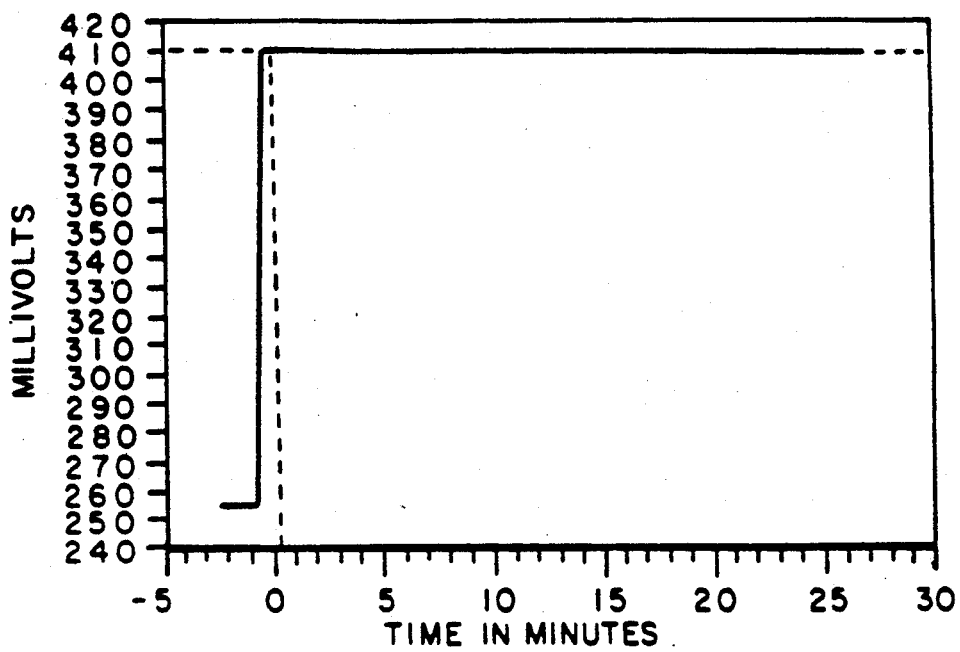

FIG. 15. A back titration pH response curve $IrO_2$/Ir/Ti/Au/Ti/Cermet in Ceramic Indicator Electrode for pH 7.33 to 4.96.

Figure 16:
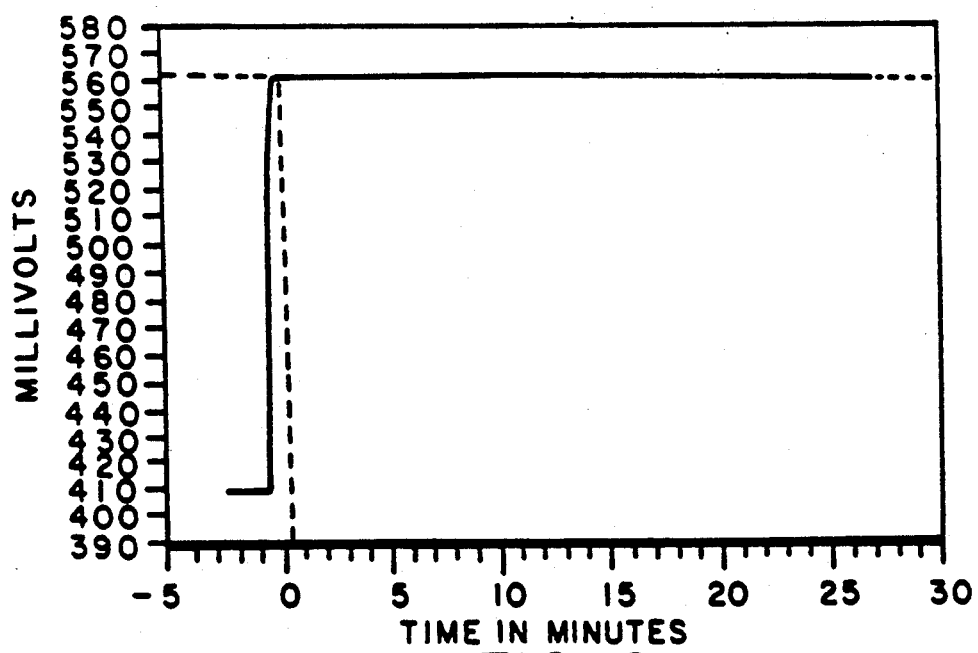

FIG. 16. A back titration pH response curve for $IrO_2$/Ir/Ti/Au/Ti/Cermet in Ceramic Indicator Electrode for pH 4.68 to 2.39.

Figure 17:
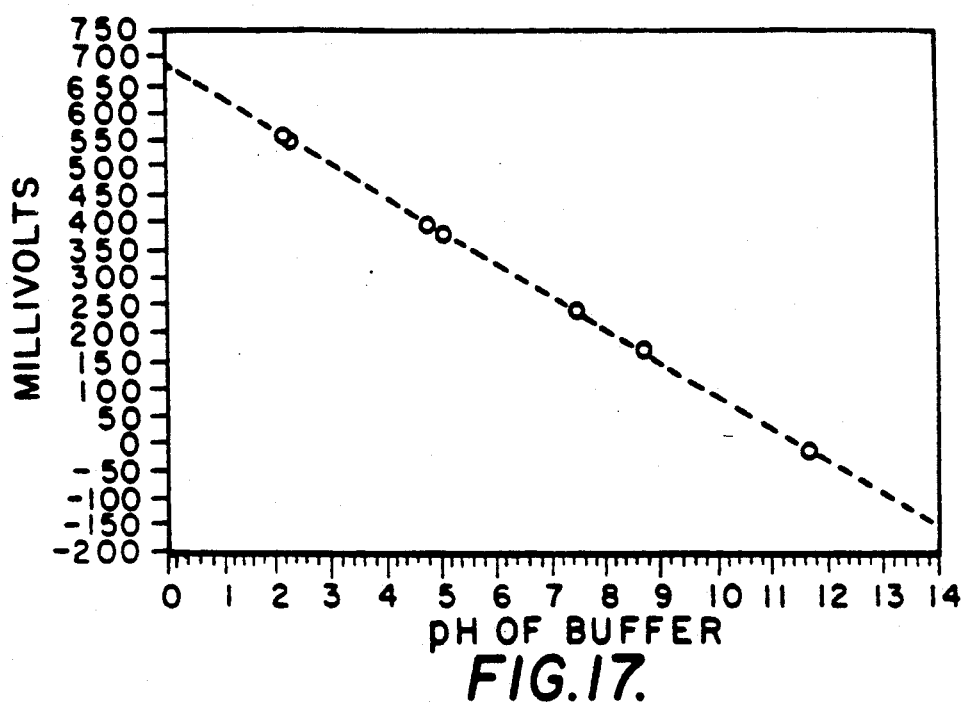

FIG. 17. Nernst plot for $IrO_2$/Ir/Ti/Au/Ti/Cermet in Ceramic Indicator Electrode.

Figure 18:
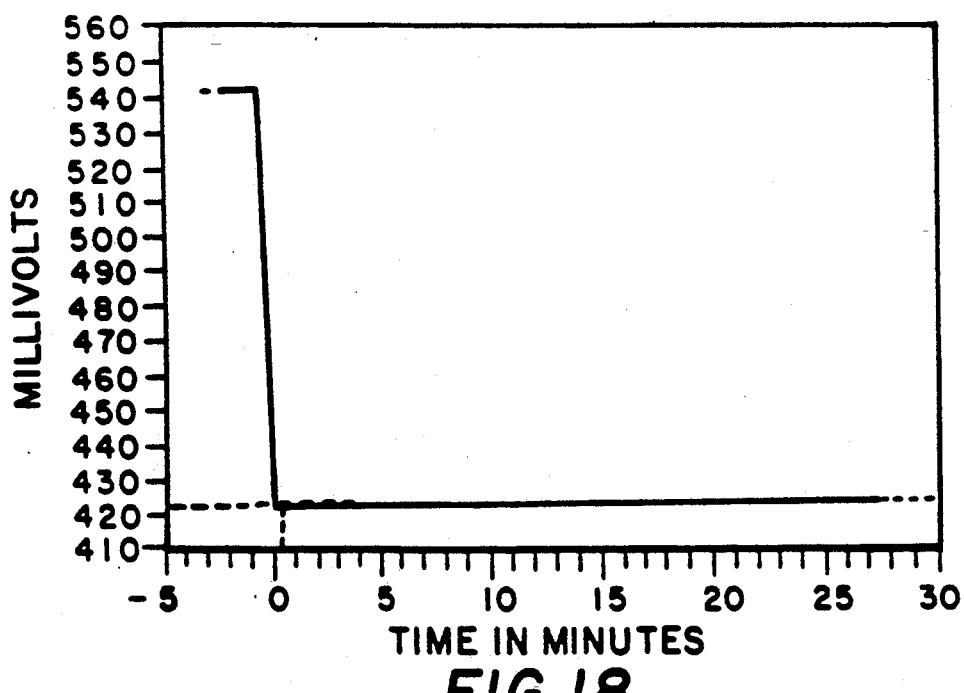

FIG. 18. pH response curve for $IrO_2$/Ir/Ti/Au/Ti/Hastelloy C pin in S-glass Indicator Electrode for pH 2.33 to 4.30.

Figure 19:
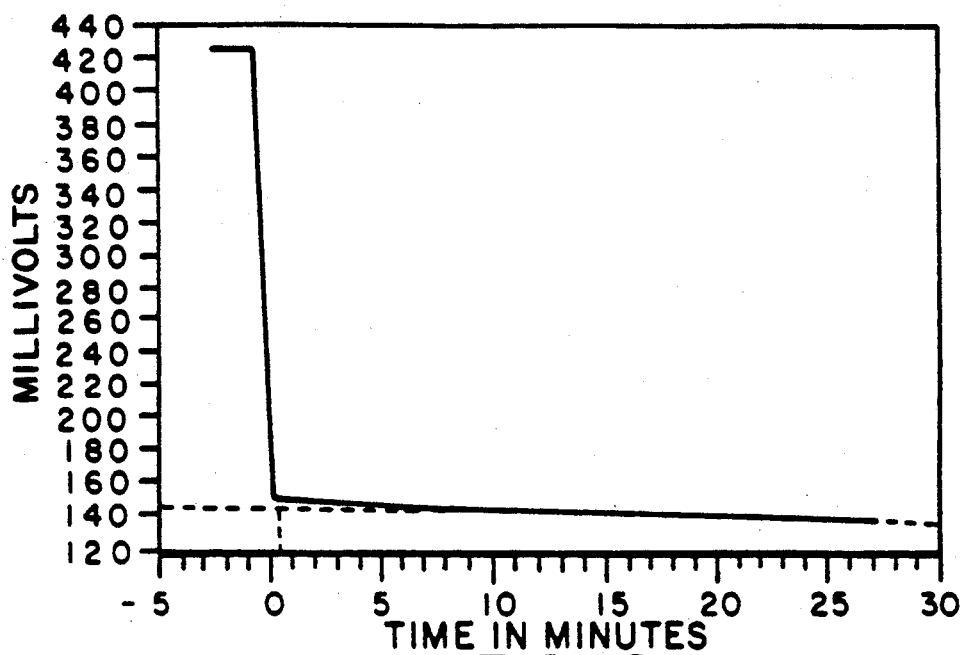

FIG. 19. pH response curve for $IrO_2$/Ir/Ti/Au/Ti/Hastelloy C pin in S-glass indicator Electrode for pH 4.61 to 8.89.

Figure 20:
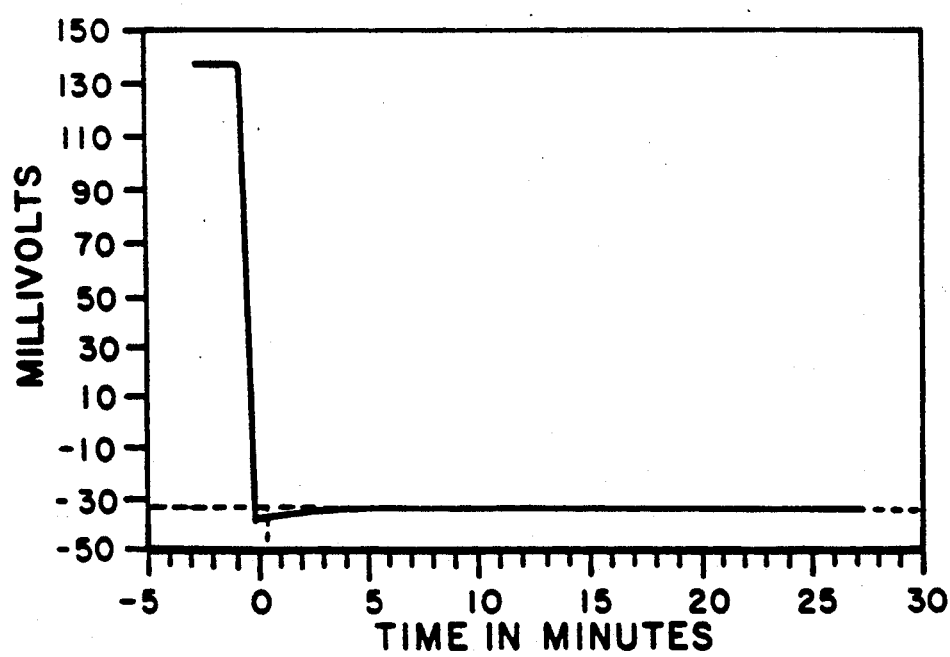

FIG. 20. pH response curve for $IrO_2$/Ir/Ti/Au/Ti/Hastelloy C pin in S-glass Indicator Electrode for pH 9.07 to 11.71.

Figure 21:
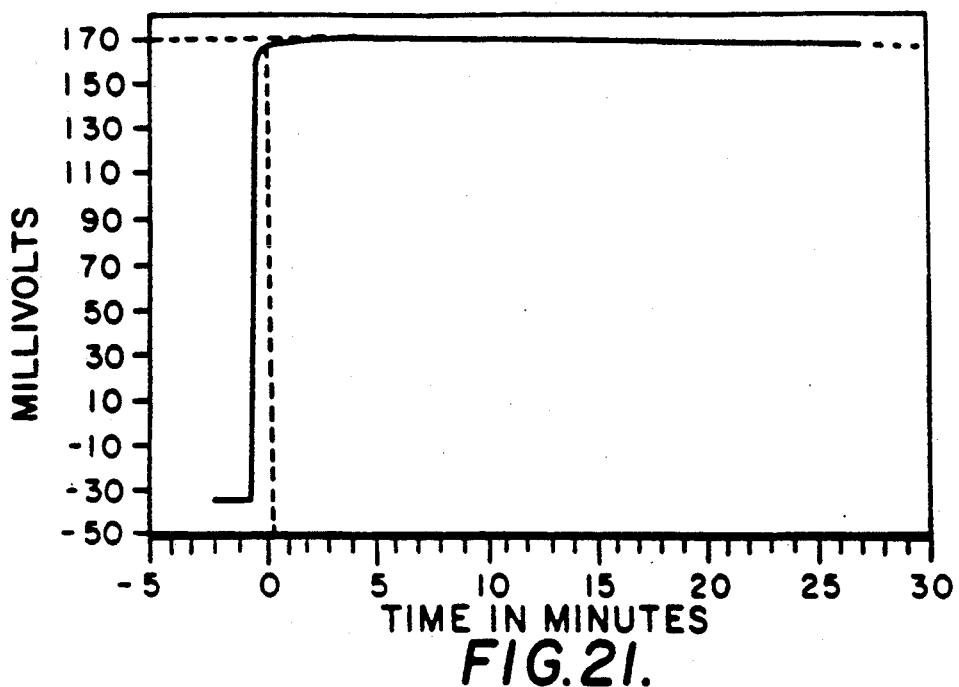

FIG. 21. A back titration pH response curve for $IrO_2$/Ir/Ti/Au/Ti/Hastelloy C pin in S-glass Indicator Electrode for pH 11.38 to 8.42.

Figure 22:
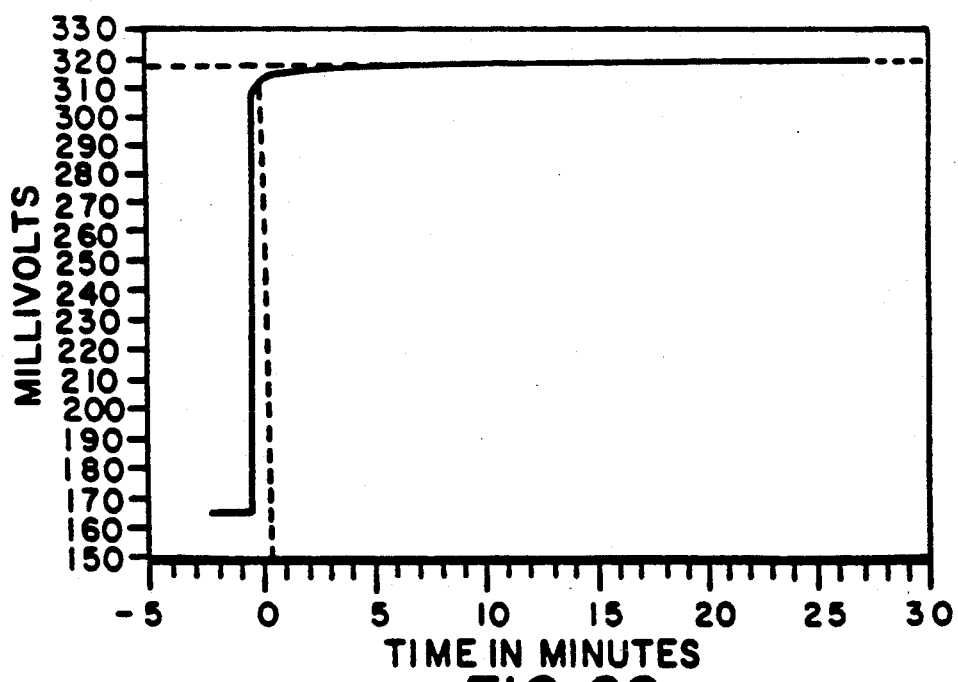

FIG. 22. A back titration pH response curve for $IrO_2$/Ir/Ti/Au/Ti/Hastelloy C pin in S-glass Indicator Electrode for pH 8.30 to 5.96.

Figure 23:
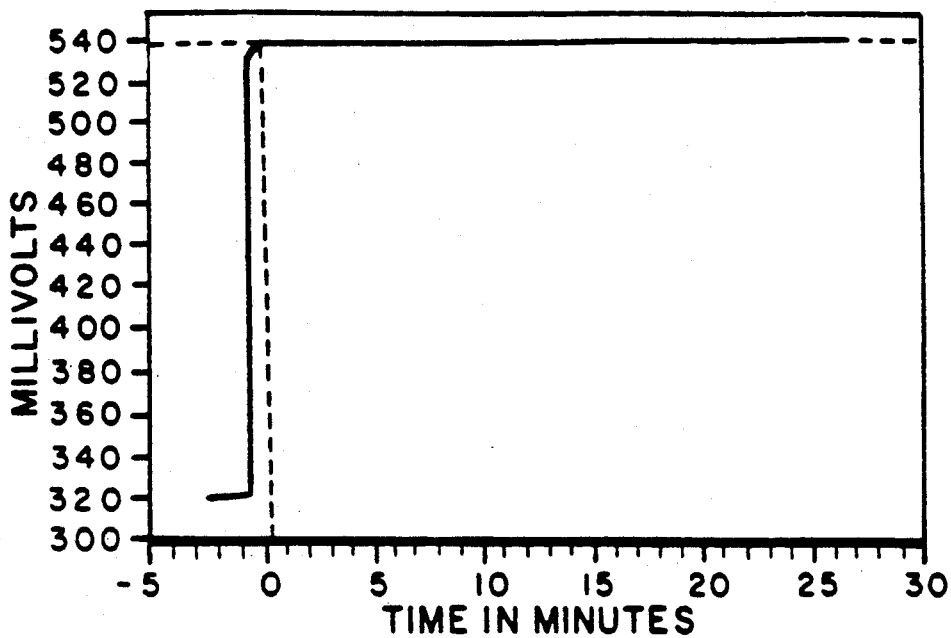

FIG. 23. A back titration pH response curve for $IrO_2$/Ir/Ti/Au/Ti/Hastelloy C pin in S-glass Indicator Electrode for pH 5.36 to 2.32.

Figure 24:
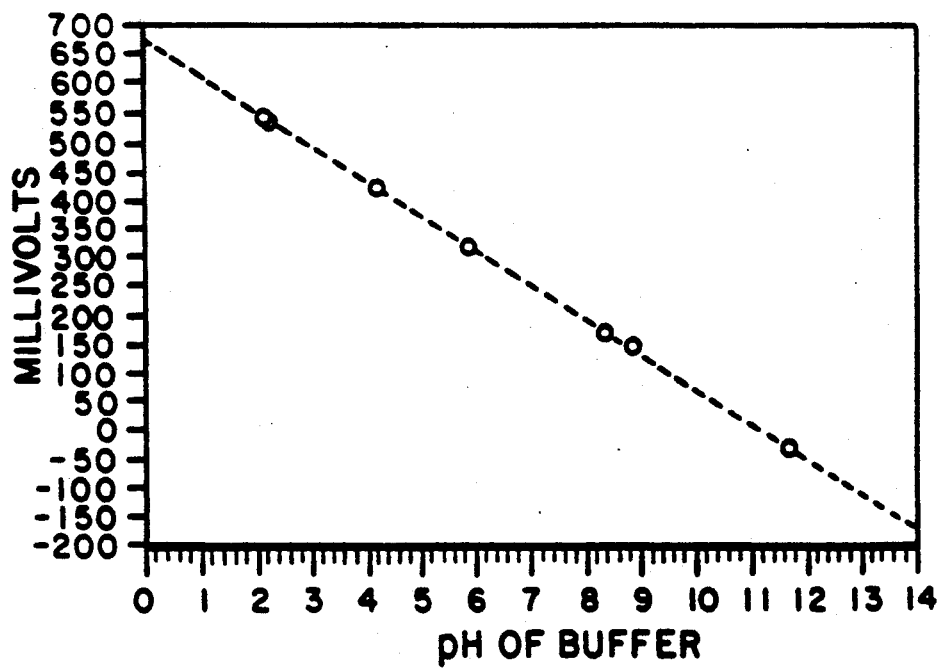

FIG. 24. Nernst plot for $IrO_2$/Ir/Ti/Au/Ti/Hastelloy C pin in S-glass Indicator Electrode.

Figure 25:
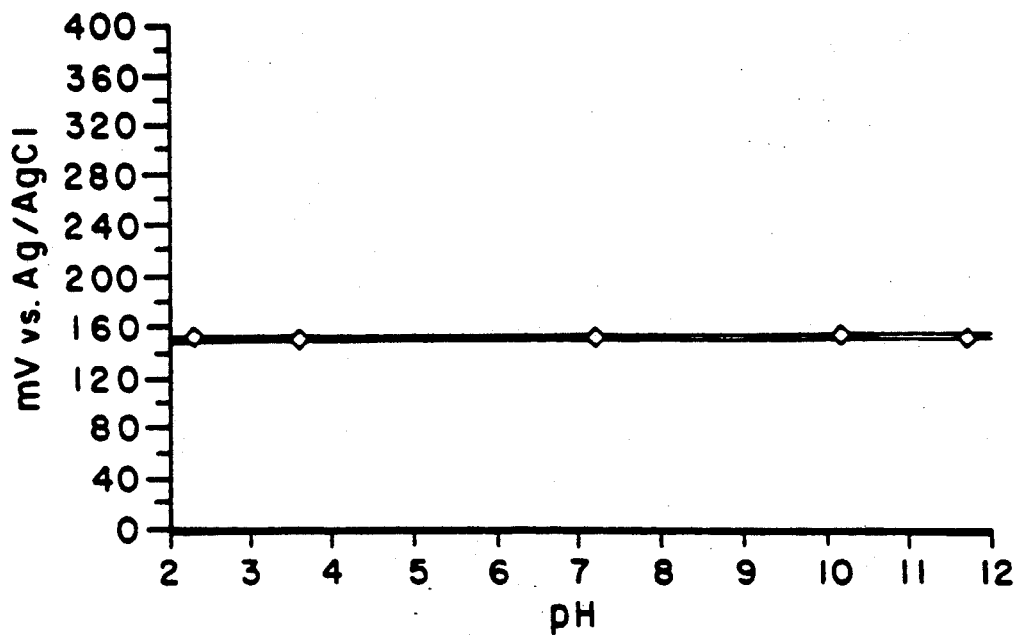

FIG. 25. pH stability plot for AgCl/Ag/Au/Cermet reference electrode coated with partially quaternized polymer and an annealed perfluorocarbon copolymer.

Figure 26:
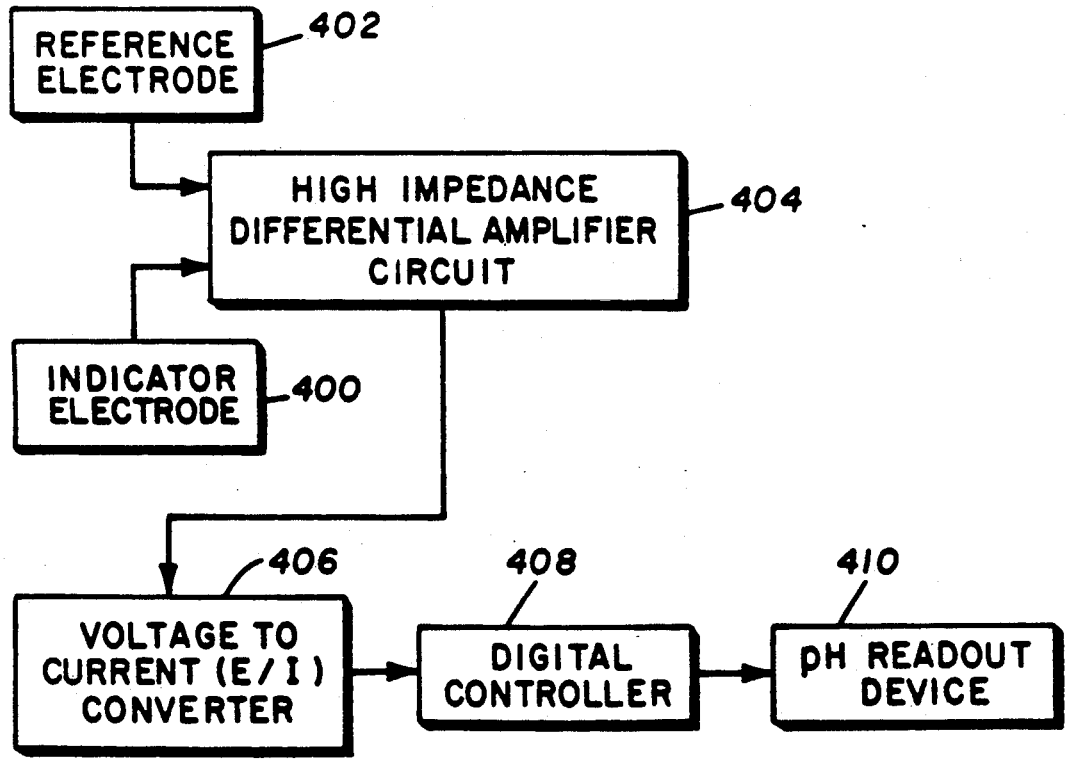

FIG. 26. Block diagram of a digital multimeter system incorporating a high impedence differential amplifier circuit.

Figure 27:
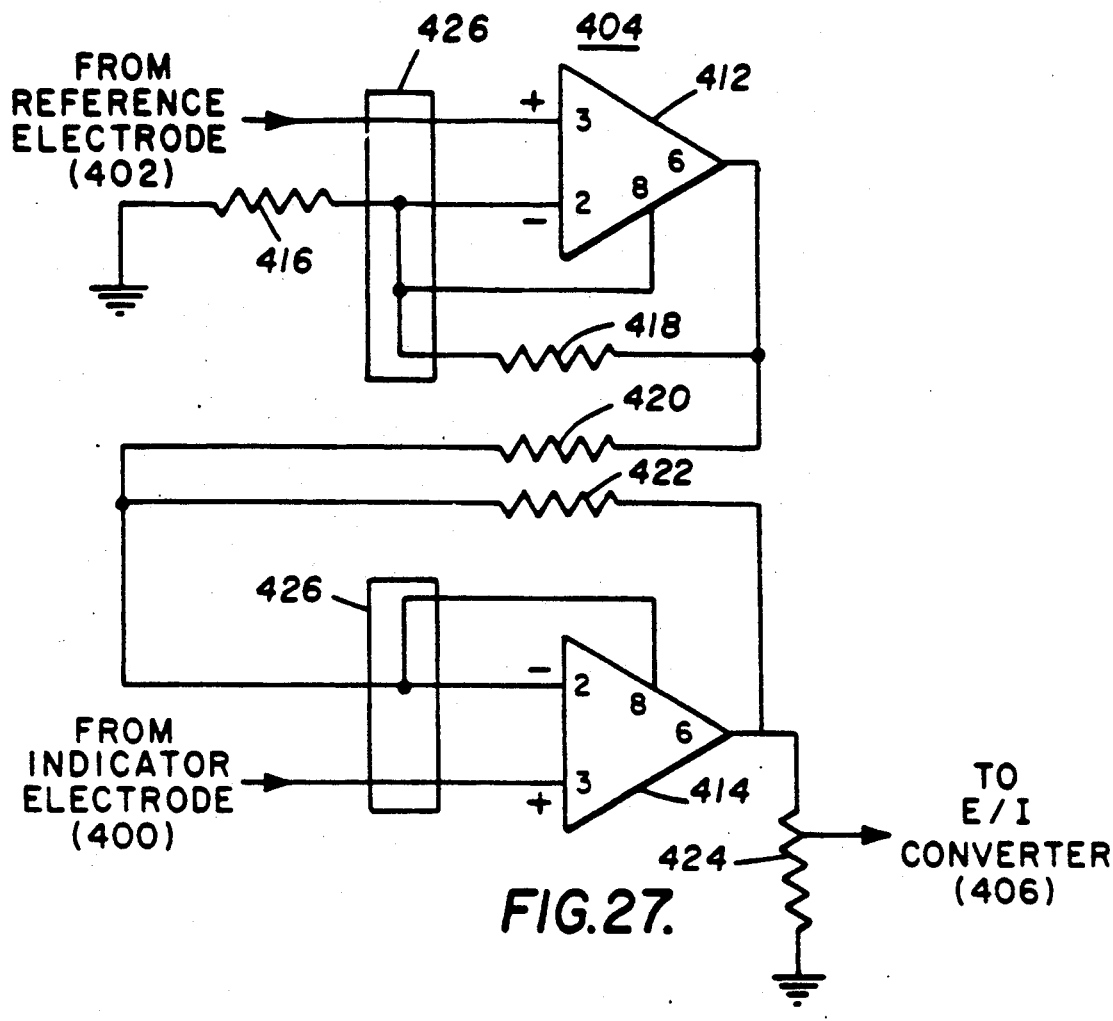

FIG. 27. A schematic of the high impedence differential amplifier circuit.

Figure 28:
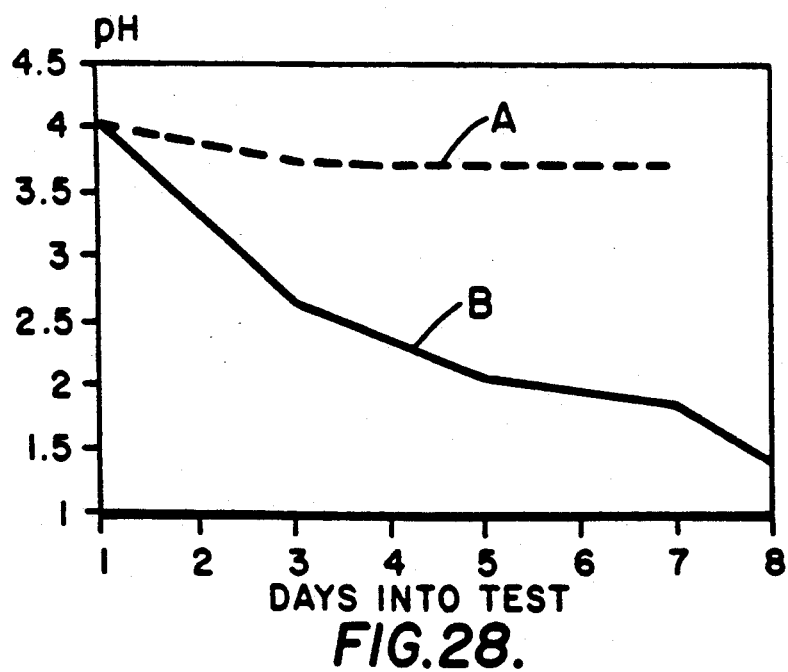

FIG. 28. Plot of drift in potential (pH units) versus time (days) for a pH sensor using a digital multimeter with (Line A) and without (Line B) a high impedance differential amplifier circuit.

DESCRIPTION

Figure 1:
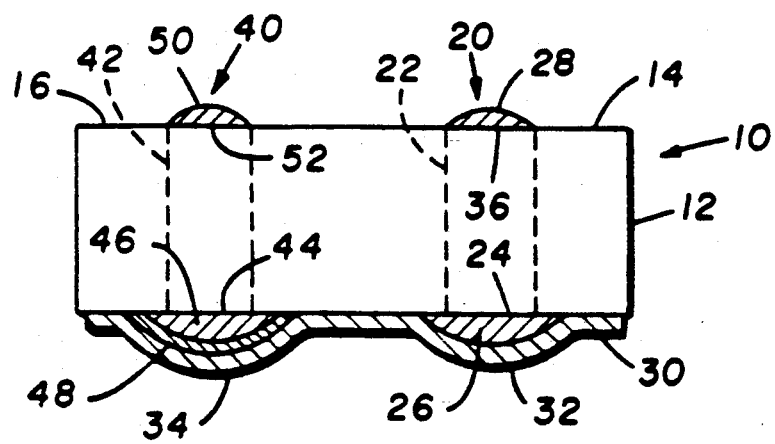
FIG. 1 is a side elevation sectional view of a solid state pH sensor embodying the concepts of the present invention, wherein the indicator and reference electrodes thereof utilize a common ceramic substrate.

Referring now to the drawings in which like numerals denote similar elements, and more particularly to FIG. 1, there is shown by way of illustration, but not of limitation, a solid state pH sensor (10) for pH sensing equipment (not shown). The pH sensor (10) comprises a ceramic substrate (12) as an electrically non-conductive substrate, an indicator electrode (20) and a reference electrode (40). The indicator electrode (20) and the reference electrode (40) are electrically insulated from each other, in part via the ceramic substrate (12).

The ceramic substrate (12) has a first cermet conductor (22) and a second cermet conductor (42) as electrically conductive conductors imbedded therein. The first cermet conductor (22) has a first cermet conductor exposed portion (24). Similarly, the second cermet conductor (42) has a second cermet conductor exposed portion (44). Preferably, these two exposed portions (24) and (44) are on the same surface of the ceramic substrate (12).

The ceramic substrate (12) may comprise any one or mixture of ceramic materials. By "ceramic material" it is intended a highly stable material which is substantially electrically non-conductive and has a crystalline structure consisting of metal and non-metal elements. The non-metal element is commonly and preferably oxygen although it may be carbon or nitrogen. Some of the common metals used as the metal element thereof are aluminum, silicon, magnesium, beryllium, zirconium, titanium, boron and combinations thereof. Examples of suitable ceramic materials would include, but are not limited to, oxides, borides, nitrides, carbides and silicides of the above-mentioned metals; and mixture thereof. The above-mentioned oxides are preferred, with alumina (oxide of aluminum; $Al_2O_3$) and S-glass particularly preferred. See *Materials Handbook*, 12th Edition, McGraw-Hill Book Company, pages 170-172 (Ceramics), 1986, which is hereby incorporated by reference.

The cermet conductor (22) and (42) may comprise any one or mixture of cermet materials. Additionally, the cermet conductors (22) and (42) may be of the same or different cermet material. By "cermet material" it is intended a material consisting of ceramic and metallic phases intimately dispersed within one another, such that an electrically conductive material is produced. See *Materials Handbook*, 12th Edition, McGraw-Hill Book Company, pages 172-173 (Cermets), 1986, which is hereby incorporated by reference. The cermet material preferably has a thermal expansion coefficient sufficiently similar to that of the ceramic material, so that the cermet conductors (22) and (42) will not separate from or crack the ceramic substrate (12) when subject to temperature changes. The same is true in general that it is preferable to substantially match the thermal expansion coefficients of the electrically conductive conductor(s) and the electrically non-conductive substrate(s). Examples of suitable cermet materials include ceramic materials such as those previously indicated herein. Examples of suitable electrically conductive metals include, but are not limited to, molybdenum, tantalum, tungsten, platinum, palladium, rhodium, titanium, gold, silver, nickel, copper, iron, aluminum, alloys thereof, and mixtures thereof. The ratio of the electrically conductive metal to the ceramic material in the cermet conductors (22) and (42) can vary widely, in the range of about 1:2 to about 4:1 based on weight. A preferred cermet material is a molybdenum/alumina cermet in a ratio of about 1:2 to about 2:1, more preferably 1:1, based on weight.

In an another embodiment, metal pins may be substituted for the cermet conductors (22) and (42). The metal pins would be of an electrically conductive metal such as those indicated above. Again, the metal pins preferably have a thermal expansion coefficient sufficiently similar to that of the ceramic material, so that the metal pins will not separate from or crack the ceramic substrate (12) when subjected to temperature changes.

The indicator electrode (20) comprises a metal/metal oxide coating (26) in electrically conductive contact with the first cermet conductor (22). As depicted in FIG. 1, the metal/metal oxide coating (26) is preferably on the first cermet conductor exposed portion (24), such that the metal/metal oxide coating (26) entirely covers the exposed portion (24). The metal/metal oxide combination utilized in the coating (26) is one suitable for use in junction-type indicator electrodes. Suitable metals for metal/metal oxide combinations would include, but are not limited to, palladium, rhodium, ruthenium, osmium, iridium, platinum, tin, antimony, bismuth, alloys thereof, and mixtures thereof. Suitable metal oxide for the metal/metal oxide combinations would include, but are not limited to, the metal oxides corresponding to the above indicated metals. The metal for the metal portion of this combination may be the same or different from the metal, preferably the same metal, of the metal oxide in the combination. In a preferred embodiment, the metal/metal oxide coating (26) utilizes the combination of iridium/iridium oxide. In an alternate embodiment, the $IrO_2$ may be RF sputtered directly onto the surface of the cermet conductor which has preferably been smoothened by, for example, diamond paste polishing and the metal, e.g. iridium, eliminated. See Canadian Pub. No. 1,219,632, page 13, lines 19-12.

If the metal oxide of the metal/metal oxide coating (26), or metal oxide coating, tends to promote the oxidation of the metal in the cermet conductor (22), or the metal pin, a barrier layer of a metal resistant to such oxidation, for example, a noble metal (such as gold) is preferably placed between the cermet conductor (22) and the metal/metal oxide coating (26) to inhibit such oxidation. If the barrier layer does nor adhere well to the cermet conductor (22), or metal pin, or if the metal/metal coating (26), or metal oxide coating, does not adhere well to the barrier layer, an adhesion layer of a metal which adheres well to both may be utilized, for example, titanium and chromium, thereby enhancing the adhesion therebetween. The adhesion and barrier layers may be applied by thin or thick film techniques.

The metal/metal oxide coating (26) is preferably coated with a first portion (32) of a perfluorocarbon copolymer coating (30), such that the first portion (32) entirely covers the metal/metal oxide coating (26). The first portion (32) acts as a barrier to the migration of anions, but not as to cations, from the environment of interest to the indicator electrode (20). The migration of anions to the indicator electrode (20) can cause interferences in the pH measurement of the environment being studied.

The reference electrode (40) comprises a metal/metal salt coating (46) in electrically conductive contact with the second cermet conductor (42), or metal pin. As depicted in FIG. 1, the metal/metal salt coating (46) is preferably on the second cermet conductor exposed portion (44), such that the metal/metal salt coating (46) entirely covers the exposed portion (44). The metal/metal salt combination utilized in the coating (46) are those suitable for use in junction-type reference electrodes. The metal/metal salt coating (46) comprises an electrically conductive layer of a metal in electrically conductive contact with a layer of a salt of the metal. The metal is preferably selected from one which readily forms an insoluble or poorly soluble salt, preferably an insoluble salt, and has good electrical properties. Examples of such conductive metals are silver, mercury and amalgams with silver being particularly useful and preferred.

The metal/metal salt coating (46) may further comprise a precoating of an electrically conductive substrate. Such a precoating is preferably utilized when improved adhesion to the ceramic/cermet surface of the ceramic substrate (12) and the second cermet conductor expose portion (44), or metal pin, is desired. Such a precoating would be an adhesion layer of a metal which adheres well to both and is electrically conductive, for example, titanium and chromium, thereby enhancing the adhesion therebetween. If the metal of the cermet conductor (42), or metal pin, tends to be anionically attacked by the anion (electrolyte) of the metal salt and of the reference electrolyte source for the reference electrode, a barrier layer of metal resistant to such anionic attack and electrically conductive, for example, a noble metal (such as gold) is preferably placed between the cermet conductor (42) and the metal/metal salt coating (46) to inhibit such anionic attack. An adhesion layer may also be utilized between the cermet conductor (42) and the barrier layer, if utilized. For example, an adhesion layer of titanium may be utilized with a barrier layer of gold. The adhesion and barrier layers may be applied by thin or thick film techniques.

Often, the ceramic/cermet surface causes certain metals, e,g., silver, to form dendrites, i.e., pores and cavities are found in large numbers, when electroplated thereon. As a result, these certain metals do not adhere to ceramic or cermet surfaces. When using these metals, dentrite formation may be avoided by first sputtering the metal onto the surface to be electroplated and then electroplating the metal thereon. The thin layer of sputtered metal provides a better nucleating surface for electroplating metal thereon. Alternatively, dendrite formation may be avoided by using thick film techniques such as using a metal paint or paste which is subsequently buffed.

The metal/metal salt combination utilized in coating (46) is preferably a metal/metal halide or a metal/metal sulfide, more preferably a metal/metal halide and yet more preferably a silver/silver halide. While bromides, chlorides and iodides may be employed as the halide of the metal halide, the metal/metal chloride is preferred, with silver/silver chloride combination being particularly preferred.

The metal/metal salt coating (46) is placed in contact with a reference electrolyte source containing a known amount of the anion of the metal salt, thereby providing a constant potential. The reference electrolyte source may be, for example, an aqueous solution of known anion concentration; a dried electrolyte layer as disclosed in U.S. Pat. No. 4,214,968 (Battaglia et al.), the disclosure of which is hereby incorporated by reference; and an immobilized electrolyte as disclosed in U.S. Pat. No. 4,908,117 (Kinlen et. al.) and assigned to the same assignee as this invention, the disclosure of which is hereby incorporated by reference.

As depicted in FIG. 1, the metal/metal salt coating (46) is preferably coated with an immobilized electrolyte coating (48), such that the immobilized electrolyte coating (48) entirely covers the metal/metal salt coating (46). A second portion (34) of the perfluorocarbon copolymer coating (30) is preferably coated onto the immobilized electrolyte coating (48), such that the second portion (34) entirely covers the immobilized electrolyte coating (48). The second portion (34) eliminates, or at least minimizes, the migration of the electrolytes (anions) in the immobilized electrolyte coating (48) away from the metal salt portion of the metal/metal salt coating (46), thereby assisting in the maintenance of a constant potential for the reference electrode (40).

The immobilized electrolyte coating (48) comprises a polymer which is at least cationic, such as quaternary ammonium polymers. Suitable polymers for conversion into cationic polymers include halogenated polymers and amine polymers. What is meant by a halogenated polymer is any halogenated polymer wherein the halogen is susceptible to nucleophilic displacement by a tertiary amine, such as polyvinyl benzyl chloride or polyphosphonitrillic chloride. Other types of halogenated polymers include chloromethylated vinylaromatics and polyvinyl chlorides. Such halogenated polymers can be quaternized by any known method of quaternization with a tertiary amine, such as exposing to tertiary amine vapors or soaking in a tertiary amine solution. The quaternized polymer can then be contacted with the metal/metal salt coating (46). Alternatively, the halogenated polymer can be contacted with the metal/metal salt coating (46) and then quaternized in situ by any of the above methods.

Conversely, amine polymers may be used, which can be quaternized using halogenated compounds to form quaternary amines. The amines must be such that they do not complex with the metal of the reference electrode (40). Tertiary amine polymers are suitable, such as p-dimethylamino polystyrene. The amine must be capable of nucleophilic displacement reaction with the halogenated compound.

The quaternized polymer must be of sufficient molecular weight to form a film or coating on the metal/metal salt coating (46), typically in the range of about 5,000 to about 150,000 daltons. The polymer also is selected to form a film on the metal/metal salt coating (46) such that the perfluorocarbon copolymer coating (30) will adhere to the immobilized electrolyte coating (48). Additionally, the polymer is selected to maximize the concentration of electrolyte in contact with the metal salt of the reference electrode (40) to generate a measurable, stable potential. Insufficient electrolyte will result in interferences from contaminates in the polymer or drift in potential. The preferred halogenated polymer is polyvinylbenzyl chloride, which is a readily available commercial polymer and is easily quaternized.

The perfluorocarbon copolymers utilized in the perfluorocarbon coating (30) are cation exchange polymers which act as a barrier to the migration of anions to the indicator electrode and away from or to the immobilized electrolyte coating (48) of the reference electrode (40) which can cause interferences when measuring pH. Such interferences are characterized by scatter in pH data or no response of the electrode with change in pH. The perfluorocarbon copolymers are preferably annealed so as to improve their permselectivity, i.e., the ability of the polymer to act as a barrier to anions and as a transport for cations.

The annealing procedure involves a heat treating step and a subsequent cooling step. The heat treating step effects a change in the molecular configuration of the copolymer to a molecular configuration which enhances the rejection of hostile or interfering anions by the copolymer. The cooling step is effected such that the molecular configuration attained in the heat treating step is preserved, particularly avoiding contraction and cracking or rapid crystallization of the annealed coating. The change in molecular configuration of the copolymer is detectable by wide-angle X-ray diffraction and manifests itself as a more highly ordered molecular configuration over the non-annealed copolymer coating.

Suitable perfluorocarbon copolymers comprise at least two monomers with one monomer being selected from a group including vinyl fluoride, hexafluoropropylene, vinylidene fluoride, trifluoroethylene, chlorotrifluoroethylene, perfluoro (alkylvinyl ether), tetrafluoroethylene and mixtures thereof.

The second monomer contains an $-SO_2F$ or $-COF$ group. Examples of such second monomers can be represented by the formula $CF_2=CFR_1SO_2F$ or $CF_2=CFR_1COF$. $R_1$ in the generic formula is a bifunctional perfluorinated radical having from 1 and 25 carbon atoms. A preferred monomer has from 1 to 8 carbon atoms. One restraint upon the generic formula is a requirement for the presence of at least one fluorine atom on the carbon atom adjacent the $-SO_2F$ or $-COF$ group. The $R_1$ generic formula portion can be of any suitable or conventional configuration, but it has been found preferably that the vinyl radical comonomer join the $R_1$ group through an ether linkage.

Typical sulfonyl or carbonyl fluoride containing monomers are set forth in U.S. Pat. Nos. 3,282,875; 3,041,317; 3,560,568 and 3,718,627, which are hereby incorporated by reference, and methods of preparation of intermediate perfluorocarbon copolymers are set forth in U.S. Pat. Nos. 3,041,317; 2,393,967; 2,559,752 and 2,593,583, which are hereby incorporated by reference.

The base copolymers are then converted to the perfluorocarbon copolymer utilized herein containing $-SO_3M$ or $-CO_2M$ groups via, for example, hydrolysis, wherein M is hydrogen, an alkali metal, an amine, an ammonium ion or salt, or an alkaline earth metal. The converted copolymer contains sulfonate or carboxylate group based ion exchange sites contained in side chains of the copolymer and attached to carbon atoms having at least one attached fluorine atom. Not all sulfonyl or carbonyl groups within the base copolymer need be converted. The conversion may be accomplished in any suitable or customary manner such as is shown in U.S. Pat. Nos. 3,770,547 and 3,784,399, which are hereby incorporated by reference.

Suitable perfluorocarbon copolymers are commercially available from E. I. du Pont de Nemours and Co., Wilmington, Del. under the trademark Nafion ®.

The indicator electrode (20) and the reference electrode (40) each further comprises an area or zone whereby electrical contact may be made between the respective electrode, (20) and (40), and the pH sensing equipment or instrumentation. These electrical leads may be placed in electrical contact with these contact zones by any suitable manner, for example, by affixing an electrical lead to another exposed portion of the imbedded cermets (22) and (42), by implanting an electrical lead in the ceramic substrate (12) in electrically conductive contact with the respective imbedded cermets (22) and (42), by drilling in hole through the ceramic substrate (22) to the respective imbedded cermet (22) and (42) and then affixing an electrical lead in electrically conductive contact with the respective cermet (22) and (42), or by attaching an electrical lead to a spring-loaded pin, which pin is urged toward and makes contact with the other exposed portion of the respective cermet conductor (22) and (42), or metal pin.

Figure 2:
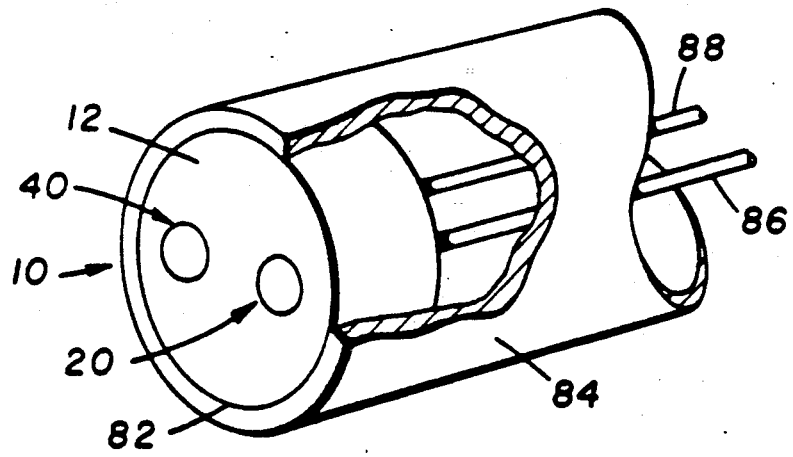
FIG. 2 is a perspective, partially sectional view of the solid state pH sensor of FIG. 1 seal-lessly attached to a housing.

As depicted in FIG. 1, the indicator electrode (20) has an indicator contact zone (28) which is electrically connected to the first cermet conductor (22) by coating another exposed portion (36) of the first cermet conductor (22) with an electrically conductive metal. The metal coating may be applied by thin or thick film techniques. An electrical lead (86), as shown in FIG. 2, may be suitably affixed to the indicator contact zone (28).

In like manner, the references electrode (40) has a reference contact zone (50) which is electrically connected to the second cermet conductor (42) by coating another exposed portion (52) of the second cermet conductor (42) with an electrically conductive metal. Again, this metal coating may be applied by thin or thick film techniques. An electrical lead (88), as shown in FIG. 2, may be suitably affixed to the reference contact zone (50).

The combination of the indicator electrode (20) and the reference electrode (40) form a pH sensor (10). The sensing portion of the pH sensor (10) is preferably coated with an ion-selective membrane, preferably a perfluorocarbon copolymer coating (30) which is preferably annealed. The pH sensor (10) has an indicator and reference contact zone, (28) and (50) respectively, for electrical contact. The electrode (20) and (40) together define an electrical potential between them when the electrodes (20) and (40) are contacted with a solution or electrolyte. By measuring the electrical potential difference between the indicator electrode (20) and the reference electrode (40) at the indicator and reference contract zones (28) and (50), as the pH sensor (10) is successively immersed in electrolyte of a different pH, a relationship between a voltage difference between electrodes (20) and (40) and the pH of a particular electrolyte in contact with the electrodes (20) and (40) can be established. The pH of electrolyte can be determined from this voltage difference.

Typically, the contact zones (28) and (50) are electrically insulated and water-proofed. In a preferred embodiment as depicted in FIG. 2, the pH sensor (10) has been attached to a housing (84). The attachment is preferably performed in a seal-less manner, for example, via laser welding or metallizing and brazing the ceramic substrate (12) to the housing (84) producing a weld joint (82). The housing (84) may be of any suitable material, for example, ceramic, cermet or metallic. The electrical leads (86) and (88) are placed in electrical contact with the indicator contact zone (28) and the reference contact zone (50), respectively, prior to seal-lessly attaching the pH sensor (10) to the housing (84). The leads (86) and (88) are attached to the pH sensing equipment (not shown), thereby making electrical contact between the first and second cermet conductors, (22) and (42) respectively, and the pH sensing equipment (not shown).

The housing (84) together with the ceramic substrate (12) and the impervious cermet conductors (22) and (42) serve to chemically and electrically insulate the indicator contact zone (28), the reference contact zone (50) and the leads (86) and (88) from the environment into which the sensor (10) is placed. As such, secondary electrochemical reactions between the environment and these insulated areas are avoided, thereby maintaining the integrity of the pH determination.

The pH sensing equipment may be any suitable or conventional electrical device for measuring electrical output, or for comparing electrical output of an indicator electrode to a reference electrode. Typically, a pH sensor using the indicator and reference electrodes of the present invention would produce electrochemical potentials ranging from $-1.00$ volts to $+1.00$ volts depending on the pH of the particular electrolyte. An electrical sensing device used with the present invention must be capable of distinguishing small voltage changes used in that range.

Figure 3:
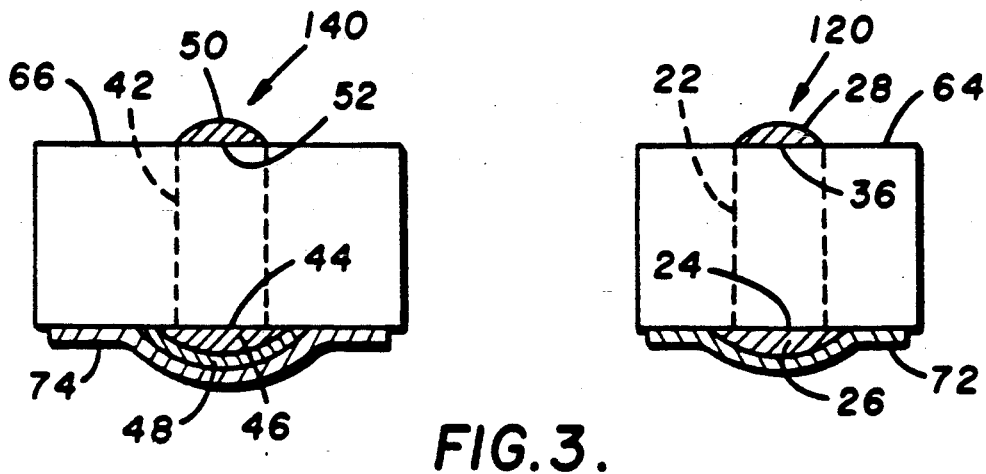
FIG. 3 is a side elevation sectional view of a solid state pH sensor embodying the concepts of the present invention, wherein the indicator and reference electrodes thereof utilize separate ceramic substrates.

In FIG. 3, there is depicted an alternative embodiment of the present invention wherein a first ceramic substrate (64) and a second ceramic substrate (66) are substituted for the first ceramic portion (14) and the second ceramic portion (16) of the ceramic substrate (12) in FIG. 1, respectively. Additionally, a first perfluorocarbon copolymer coating (72) and second perfluorocarbon copolymer coating (74) are substituted for the first perfluorocarbon copolymer portion (32) and the second perfluorocarbon copolymer portion (34) of the perfluorocarbon copolymer coating (30) in FIG. 1, respectively. As a result, a separate indicator electrode (120) and a separate reference electrode (140) are formed corresponding to the indicator electrode (20) and the reference electrode (40) of the pH sensor (10) of FIG. 1. Like the pH sensor (10) in FIG. 2, the separate indicator and reference electrodes (120) and (140), respectively, may be individually attached to their own housing (not shown) with their corresponding electrical leads (not shown).

Figure 4:
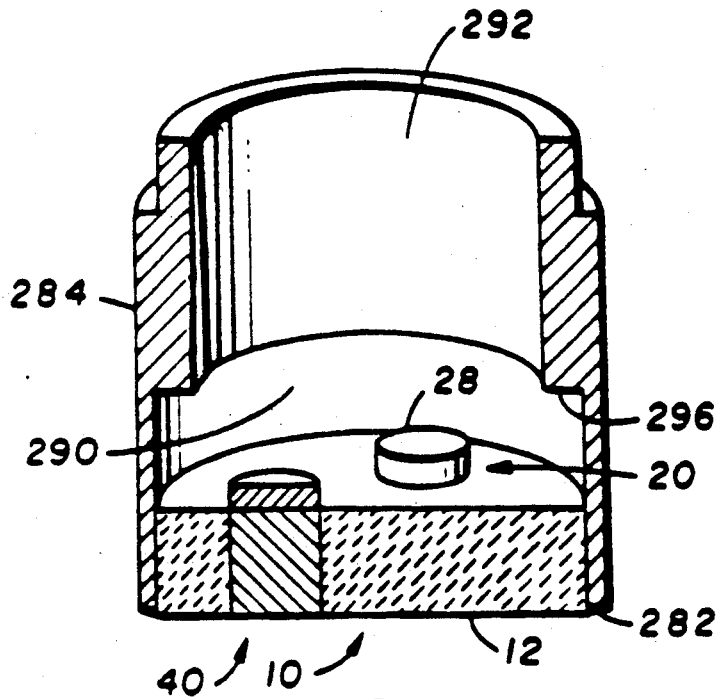
FIG. 4 is a side elevation sectional view of a ceramic/cermet header seal-lessly attached to a housing.
Figure 5:
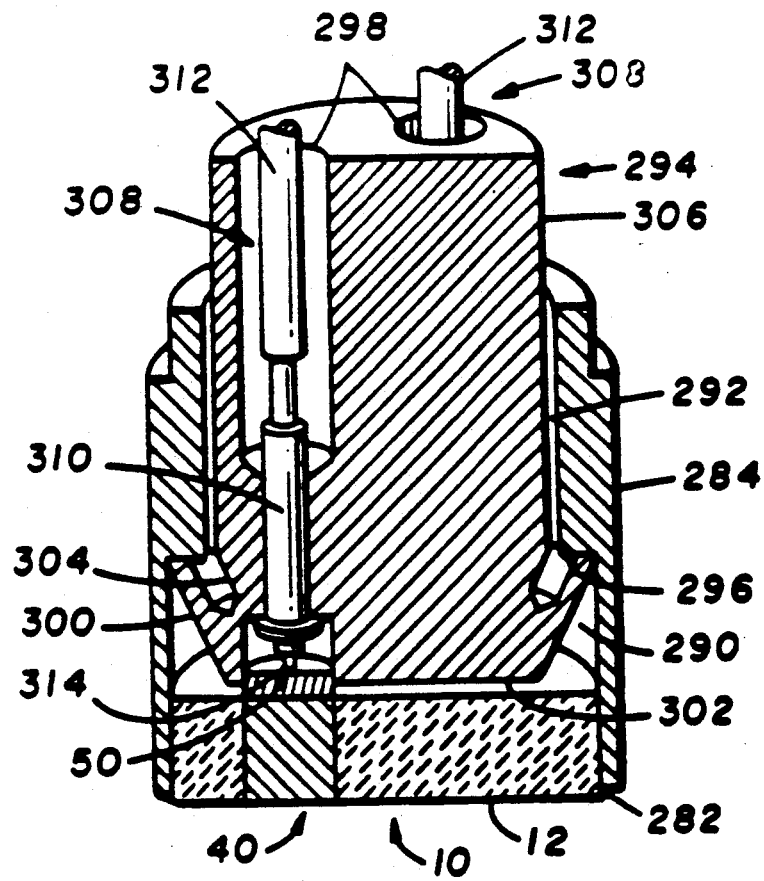
FIG. 5 is FIG. 4 further including and showing a snap-on connector with spring-loaded pin connectors.

In another preferred embodiment as depicted in FIGS. 4 and 5, the pH sensor (10) has been attached to a housing (284). As noted earlier, the attachment is preferably performed in a seal-less manner, for example, via laser welding or metallizing and brazing the ceramic substrate (12) to the housing (284) producing a weld joint (282). The housing (284) may be of any suitable material, for example, ceramic, cermet or metallic.

The housing (284) has a first portion (290) which receives the pH sensor (10) and a second portion (292) which receives a snap-on connector (294). The first portion (290) and the second portion (292) are cylindrical in shape and have a different radius with the first portion (290) having a larger radius. The transition between the first portion (290) and the second portion (292) forms a lip (296).

The snap-on connector (294) has a plurality of sockets (298) which correspond in number and location to the contact zones, for example, contact zones (28) and (40) on the pH sensor (10). The snap-on connector (294) also has a skirt section (300) which is connected to and integrally formed with the bottom face (302) of the snap-on connector (294). Other than at the bottom face (302), the skirt section (300) is spaced from the bottom section (304) of the snap-on connector (294). The bottom face (302) has the same or smaller radius than the radius of the top section (306). When the snap-on connector (294) is inserted into the second portion (294) of the housing (284), the skirt section (300) is urged toward the bottom section (304). When the skirt section (300) is within the first portion (290), the skirt section (300) assumes its expanded form and engages the lip (296) retaining the snap-on connector (294) in place.

Each socket (298) accommodates and retains a spring-loaded pin (308). The spring-loaded pin (308) has a sleeve (310), a pin (312), and a spring (not shown) within the sleeve (310). The sleeve (310) snugly fits within a portion of the socket (298) and is retained there. Once the snap-on connector (298) is placed into position within the housing (284) as shown in FIG. 5, the point (314) of the pin (312) is urged by the spring in the sleeve (310) toward the respective contact zone, for example, contact zone (50), thereby making electrical contact therewith.

Each of the pins (312) are connected to their corresponding electrical leads, for example, electrical lead (88) (not shown), which are in turn connected to the pH sensing equipment (not shown).

The separate indicator and reference electrodes (120) and (140), respectively, may be utilized together to form a pH sensor in accordance wtih the present invention or utilized individually in conjunction with the respective electrode's counterpart, such as those existing within the prior art of indicator and reference electrodes.

PREPARATION OF THE CERAMIC/CERMET COMPONENT

The ceramic substrate with the cermet conductor(s) imbedded therein for the pH sensor or the separate indicator or reference electrode of the present invention may be manufactured in various ways. For example, a finely divided metal/metal oxide mixture powder is press-molded to form a cermet conductor. Then, the cermet conductor(s) is encapsulated within a solid electrolyte member (ceramic substrate) by forming the solid electrolyte member on the exterior surface of the cermet conductor(s) by vapor deposition, ion plating, sintering, or sputtering, as disclosed in U.S Pat. No. 4,209,378. Finally, the so-formed product is sintered. The ceramic substrate may then be modified to expose at least one portion preferably two portions, of each of the cermet conductors imbedded therein.

In another technique, the finely divided solid electrolyte material for the ceramic substrate is press-molded too form a provisional ceramic member having a hole therethrough in which a cermet conductor is to be formed. Then, an amount of a finely divided metal/metal oxide mixture is charged in the hole corresponding to each of the cermet conductors therein in excess of the amount of the mixture required to fill the hole forming a mound of the mixture above the hole. Then, the metal/metal oxide mixture is pressed to obtain a structure such that each cermet conductor imbedded within the ceramic substrate has two exposed portions on opposing surfaces of the ceramic substrate. Finally, the obtained structure is sintered.

In another more preferred techniques, the finely divided solid electrolyte material for the ceramic substrate is press-molded and sintered to form a provisional ceramic member. A hole is drilled into and preferably through the provisional ceramic member corresponding to each of the cermet conductors to be formed therein. Then, as before indicated, an amount of a finely divided metal/metal oxide mixture is charged in the hole corresponding to each of the cermet conductors therein in excess of the amount of the mixture required to fill the hole forming a mound of the mixture above the hole. Then, the metal/metal oxide mixture is pressed to obtain a structure such that each cermet conductor imbedded within the ceramic substrate has at least one, preferably two, exposed portions. However, it is more preferred to form the finely divided metal/metal oxide mixture into a slurry in which the mixture is mixed with a low boiling point liquid (100° C.–150° C. b.p.), for example, butyl carbitol acetate, and optionally a surfactant to aid in maintaining a homogoneous mixture and to compact same therein. The slurry is then poured into each of the holes in the ceramic substrate until the holes are full and a small lump of excess slurry covers the holes. Filter paper may be placed below the ceramic substrate and a slight vacuum pulled through the holes from below the filter paper—again to aid in compacting the slurry within the holes so as to avoid the formation of voids within the cermet conductors. Then, the ceramic substrates are placed in an oven to slowly evaporate the solution of the slurry. The ceramic substrate is then cooled, pressed and sintered.

The resulting ceramic substrates are ground to desired thickness and uniform surface finish and then cleaned.

PREPARATION OF THE INDICATOR ELECTRODE

The process for preparing the indicator electrode involves coating the exposed portion of the first cermet conductor with a metal/metal oxide coating or a metal oxide coating which is electrically conductive which in turn is coated with the first portion of the perfluorocarbon copolymer coating and preferably annealed. The metal/metal oxide coating or the metal oxide coating may be applied by any appropriate means, such as employing one of the thin-film or thick-film techniques as disclosed in U.S. Pat. No. 4,536,274 (Papadakis et al.) and Canadian Patent No. 1,219,632 (Lauks), which are hereby incorporated by reference. Of these techniques, thin-film techniques are preferred, such as electrode deposition, brazing and sputtering, more preferably sputtering. For the metal oxide portion of the coating, a most preferred method is reactive sputtering, for example, DC Magnetron reactive sputtering or RF reactive sputtering such as disclosed by in *Deposition Technologies for Films and Coatings*, Noyes Publications, Park Ridge, N.J., pages 170–237 (Coating Deposition by Sputtering) (1982) and K. Kreider, "Summary Abstract:$IrO_2$ Radio Frequency Sputtered Thin Film Properties", J. Vac. Sci. Technol., A4(3), May/June 1986, 606, which are hereby incorporated by reference. Reactive sputtering of metal oxides is most preferred because coating thickness, morphology, and stoichiometry may be more effectively controlled utilizing this procedure.

The perfluorocarbon copolymer coating is then applied as a solution so as to completely cover the metal/metal oxide coating or the metal oxide coating. The copolymer coating is then dried. The coating and drying steps may be repeated as required to produce a coating which acts as a barrier against the migration of anions to the metal/metal oxide coating or the metal oxide coating. The copolymer coating may be applied by methods, such as spraying, vacuum deposition, dipping or spin-coating. Finally, the copolymer coating is hydrated.

Preferably, the morphology (molecular configuration) of the perfluorocarbon copolymer of this coating is changed to one which is more highly ordered as evidenced by X-ray diffraction, such as wide-angle diffraction. The more highly ordered copolymer contains functional groups, i.e., carbonyl ($-CO_3^1$) or sulfonyl ($-SO_2^{31}$) groups, that are more closely spaced than the unchanged, i.e., non-annealed, copolymer, thereby providing an enhanced functional group domain structure, thereby providing an enhanced functional group domain structure. As such, the change copolymer possesses better permselectivity than the unchanged copolymer. The annealed copolymer also possesses enhanced adhesion and lower solubility.

Various methods for effecting a change in the morphology of such copolymers are disclosed by R. B. Moore, III and C. R. Martin, "Procedure for Preparing Solution-Cast Perfluorosulfonated Ionomer Films and Membranes," Anal. Chem., 1986, Vol. 58, pp. 2569-70; G. Gebel, P. Aldebert, and M. Pineri, "Structure and Related Properties of Solution-Cast Perfluorosulfonated Ionomer Films," Macromolecules, 1987, Vol. 20, pp. 1425-1428; U.S. Pat. No. 4,089,759 (Krumpelt et al.; for free standing membranes); and U.S. Pat. No. 4,818,365 filed Oct. 14, 1986, entitled "Solid State Indicator Electrode and Method for Making Same," and assigned to the same assignee as this invention; which are hereby incorporated by reference. Moore et al. and Gebel et al. utilized a low boiling point/high boiling point co-solvent and correspondingly two-stages of heat treating. However, care should be exercised when utilizing this method in that the properties and behavior of such films are strongly dependent upon the procedure used, i.e., upon the counterions of the perfluorocarbon copolymer (acid or salt), the presence and type of additional polar solvents, and the thermal history.

The preferred procedure is the procedure disclosed in U.S. Pat. No. 4,818,365. The annealed coating of U.S. Pat. No. 4,818,365 does not form the same morphology as the annealed free-standing membranes of U.S. Pat. No. 4,089,759 (Krumpelt et al.) as evidenced by X-ray diffraction of the two annealed materials. The difference is believed to be surface effects of the material onto which the copolymer is coated. The annealed membranes exhibited one-dimensional crystallinity having a hexagonal packing of polymer chains. On the other hand, the annealed coatings exhibited two-dimensional crystallinity wherein the chains are regularly packed hexagonally and have interchain alignment on the substrates utilized herein.

More uniform properties and behavior of the annealed copolymer coating are obtained by this preferred procedure which utilizes low boiling point solvents, such as water and lower alkyl (up to $C_5$) alcohols and ethers or mixtures thereof, which may be evaporated at or less than 140° C., preferably between about room temperature and about 140° C. Care should exercised to avoid formation of a skin upon the drying copolymer to avoid trapping solvent within the coating prior to annealing the coating. Trapped solvent would be decomposed at the annealing temperatures by the acidic copolymer and impair the effective and uniform annealing of the copolymer. Once the applied copolymer coating is dried onto the metal/metal oxide coating or metal oxide coating, the copolymer coating is annealed, i.e., heat treated, at a temperature and for a time duration to effect the desired morphological transformation of the copolymer in the copolymer coating, such as the heat treatment procedure Krumpelt et al. utilized in heat treating their membranes.

In a preferred embodiment, the first cermet conductor (22) is coated by spin-coating a solution of about 5% to about 15% by weight of Nafion ® 117 perfluorocarbon copolymer of about 1100 equivalent weight in a low aliphatic (up to $C_5$) alcohol and water. The copolymer coating is then dried by any appropriate means to remove the solvent, such as by heating, air drying at room temperature, or drying in a desiccator. If heating to dry, the temperature is preferably not raised above about 140° C. so as not to disturb the molecular configuration of the copolymer (i.e., remains an unchanged or non-annealed copolymer). The preferred means of drying the copolymer coating is to heat the indicator electrode, (20) or (120), in the range from about 80° C. to about 140° C. for about 30 minutes to about 90 minutes. The coating procedure is repeated, if necessary, until the metal/metal oxide coating or metal oxide coating (26) is entirely coated with a thin film of the perfluorocarbon copolymer, i.e., coating portion (32) or coating (72), which is not thick enough to inhibit the responsiveness of the indicator electrode, (20) or (120), yet sufficient to entirely cover the metal/metal oxide coating or metal oxide coating (26). A preferred number of repetitions of the coating procedure is from 1 (i.e., the coating procedure is performed one time) to about 5 times, the most preferred number of repetitions being from 2 to 4 times.

The perfluorocarbon copolymer coating, (30) or (72), is then annealed by heat treating the coated indicator electrode to an effective temperature and for a time duration for effecting a change in the molecular configuration of the copolymer which enhances the rejection of anionic interferences and then cooling, preferably to room temperature. Although the mechanism of the molecular reconfiguration and improved rejection of interferences caused by anion migration is not understood and not wishing to be bound to any particular theory, it is believed that the annealing of the copolymer coating produces a better defined functional group domain structure, i.e., better phase separation between the functional group portion (or phase) and the non-functional group portion (or phase) of the copolymer, and a more highly ordered copolymer. Both of these factors would likely contribute to the enhanced permselectivity of the annealed copolymer coating over the non-annealed copolymer coating.

The preferred method of annealing the copolymer coating involves heating the copolymer coated indicator electrode in an oven initially at room temperature and slowly raising the oven temperature to a maximum temperature of about 250° C., preferably about 230° C. and more preferably about 210° C., for a period of time sufficient to effect the morphological reconfiguration of the copolymer. If the copolymer is subjected to a temperature in excess of about 280° C., degradation of the copolymer typically occurs. If the copolymer is subjected to a temperature of less than about 150° C., or heated an insufficient amount of time, the morphological reconfiguration has not been observed to occur. A preferred temperature range for annealing the copolymer is from about 150° C. to about 250° C., more preferably from about 180° C. to about 230° C. A time duration for annealing the copolymer at an effective temperature is at least about 15 minutes, preferably from about 15 minutes to about 11 hours, more preferably from about 15 minutes to about 2 hours and most preferably from about 15 to about 60 minutes.

The indicator electrode, (20) or (120), is then cooled by any conventional means that allows slow cooling, preferably down to room temperature. A suitable method is by turning off the oven and allowing the indicator electrode to cool slowly to room temperature in the oven over a period of about 30 to about 90 minutes. It is presently believed that if the coating is cooled too quickly, the copolymer coating may not properly maintain the desired reconfigured morphology because too rapid a cooling may cause contraction and cracking or rapid crystallization of the copolymer coating. Preferably, each application of the perfluorocarbon copolymer is flash dried, annealed and cooled.

Proper coating and annealing of the indicator electrode can be tested by cyclic voltammetry (CV) in the presence of ferricyanide. An untreated or improperly treated indicator electrode will show a reversible CV for the reduction of ferricyanide to ferrocyanide caused by migration of the anion to the indicator electrode. An indicator electrode prepared according to the present invention should show no reversible CV for ferricyanide, since that interference is effectively eliminated in that the anion is unable, or substantially unable, to migrate to the indicator electrode.

The coated indicator electrode is hydrated by means such as soaking, heating or boiling in a liquid such as water, water solutions or buffer solutions or exposure to vapors thereof (e.g., steaming). Other water sources include water-saturated air and stream. In a preferred embodiment, the indicator electrode is heated in a boiling buffer solution. The most preferred method is to boil the indicator electrode in a 0.1M solution of phosphate buffer, around pH 7, for about 15 to about 45 minutes. The indicator electrode is then allowed to cool in the solution and is stored in the buffer solution. Once the indicator electrode is hydrated, it is preferably kept hydrated by contacting it with a water source such as storing it immersed in water, buffer solution or other aqueous solutions. Other water sources include water-saturated air and steam.

PREPARATION OF THE REFERENCE ELECTRODE

The method for preparing the reference electrode involves coating the exposed portion of the second cermet conductor with a metal/metal salt coating which in turn is preferably coated with an immobilized electrolyte coating. The immobilized electrolyte coating is preferably and at least partially quaternized polymer containing an immobilized electrolyte. The immobilized electrolyte coating is then dried and preferably coated with the second portion of the perfluorocarbon copolymer coating. The perfluorocarbon copolymer coating is dried, and preferably annealed, and subsequently cooled and hydrated.

The metal/metal salt coating may be applied by any appropriate means, such as employing one of the thin-film or thick-film techniques as disclosed in U.S. Pat. No. 4,536,274 (Papadakis et al.), previously incorporated by reference herein, to apply the metal of the metal/metal salt coating to the exposed portion of the second cermet conductor. At least a portion of the metal is then reacted to produce a metal salt, thereby forming the metal/metal salt coating.

In a preferred embodiment, the metal/metal salt coating is a silver/silver chloride coating with the metal being electroplated onto the cermet. However, in cermets containing a metal content of less than about 60 percent by weight, direct electroplating of silver onto the cermet produced undesirable silver dendrites rather than a smooth, uniform plating. The foregoing may be resolved by either precoating the cermet surface with a non-dendrite forming, electrically conductive metal, such as a barrier layer with or without an adhesion layer, prior to coating with silver or, alternatively, utilizing a higher metal content cermet or a variable metal content cermet, such as that disclosed by U.S. Pat. No. 4,495,049 (Secrist et al.), which is hereby incorporated by reference, with the higher metal content portion thereof corresponding to the exposed portion of the second cermet conductor. By either of the foregoing methods, a dendrite-forming metal, e.g., silver, may be electroplated thereon to yield a smooth, uniform plating.

The applied metal of the metal/metal salt coating may be partially converted to the desired metal salt by suitable or conventional chemical or electrochemical techniques. Generally, techniques for chemically converting metal to, for example, a metal halide involve exposure or contact of the surface of the metal, for example silver, with a solution of a salt of the halide to be formed in the presence of an oxidant for a period and at a temperature sufficient to cause the desired conversion. Techniques for electrochemically converting metal to metal halide involve making the metal anodic within an aqueous electrolyte including a salt of the halide to be formed. Other useful techniques for preparing such metal/metal salt coatings are described in U.S. Pat. Nos. 3,591,482; 3,502,560; and 3,806,439; which are hereby incorporated by reference. Although the teachings of these references are directed primarily to the preparation of wire electrodes, those skilled in the art can adapt such techniques to the manufacture of electrodes constructed utilizing a thin metal film or plating on a substrate. Alternatively, a discrete layer of metal salt may be coated over the metal layer as long as appropriate contact between the metal and metal salt is maintained. See, for example, A. Belkind et al., "RF Sputtering AgCl", *Thin Solid Films*, Vol. 142, pages 113–125 (1986), which is hereby incorporated by reference.

The metal/metal salt coating of the reference electrode is then placed in contact with a reference electrolyte source containing a known amount of the anion (electrolyte) of the metal salt, thereby providing a constant potential. In a preferred embodiment, the reference electrolyte source is an immobilized electrolyte coating as disclosed in U.S. patent application Ser. No. 304,007, filed Jan. 30, 1989, a continuation of U.S patent application Ser. No. 929,879, filed Nov. 13, 1986 (now abandoned) and assigned to the same assignee as this invention and entitled "A solid State Reference Electrode," previously incorporated herein by reference.

The metal/metal salt coating may be coated with the immobilized electrolyte by methods such as spraying, vacuum deposition, dipping or spin coating. For example, a film coating is made on the metal/metal salt coating by spray-coating a solution of about 1 to about 10 percent by weight of an at least partially quaternized, preferably completely quaternized, polymer dissolved or suspended in a solvent such as THF, 2-methoxy ethanol or hexafluoroisopropanol or a mixture or such solvents. Water of ethanol may be used as a solvent for the completely quaternized polymer. The partially quaternized halogenated polymer can be prepared by any known method of quaternizing a halogenated polymer. In a preferred embodiment, polyvinylbenzyl chloride is dissolved in a polar solvent such as THF or hexafluoroisopropanol. An excess of a tertiary amine such as triethylamine is added and the solution refluxed for a period sufficient for an at least partial quaternization to occur, in the range of about 30 to about 90 minutes. The quaternized polymer is purified, washed and dried according to any conventional method, then dissolved in any of the polar solvents described above. The metal/metal salt coating is coated with the solution or suspension. The metal/metal salt coating should be sufficiently coated that upon visual inspection a continuous film or coating is observed on and entirely covering the metal/metal salt coating.

The immobilized electrolyte coating is then dried by evaporation at room temperature of the solvent. The drying process can be accelerated by heating the coated reference electrode to about 100° C. or less.

The immobilized electrolyte coating on the exposed portion of the second cermet conductor is then preferably coated with a perfluorocarbon copolymer to entirely cover the immobolized electrolyte coating. The perfluorocarbon copolymer is applied and dried in the same manner as the perfluorocarbon copolymer coated onto the metal/metal oxide coating of the indicator electrode previously disclosed herein. Preferably, the first application of the perfluorocarbon copolymer is dried quickly (flash dried) to minimize dissoluton of the quaternized polymer and mixing of the two polymers. The perflourocarbon copolymer coating on the immobilized electrolyte coating is then preferably annealed and cooled in a like manner as with the indicator electrode to effect the desired and previously disclosed morphological reconfiguration of the copolymer to enhance the permselectivity thereof. Preferably, each application of the perfluorocarbon copolymer is flash dried, annealed and cooled. Herein, the perfluorocarbon copolymer coating acts not only as a barrier against the migration of anions to the immobilized electrolyte coating, but also as a barrier against the migration of anions contained within the immobilized electrolyte coating away therefrom so as to maintain a constant reference potential.

The immobilized electrolyte and perfluorocarbon copolymer coatings of the reference electrode are then hydrated by any appropriate means such as those previously disclosed herein in reference to the indicator electrode.

The reference electrode can be examined for proper coating of the perfluorocarbon copolymer by testing for migration of the electrolyte or anions thereof away from the electrode. This examination may be performed by placing the reference electrode in deionized water for several hours and then examining for the presence of electrolyte (anion) thereof. For example, if the electrolyte is chloride, the drift in potential may be monitored, i.e., if the drift is positive, less chloride is present; and, if the drift is negative, more chloride is present. Alternatively, a drop of silver nitrate dropped into the deionized water would indicate the presence of chloride by turning cloudy or formation of a precipitate.

The following examples are for illustrative purposes only and are not meant to limit the claimed invention in any manner.

EXAMPLES

Unless otherwise specified, electrode potentials (solid state pH indicator and reference electrodes) were measured versus standard reference electrodes (silver/silver chloride or calomel) using either a Fisher Scientific Model 825 Accumet pH meter or a Model 835 Accumet pH Scanner.

EXAMPLE 1

Ceramic/Cermet Substrate

The ceramic substrate consisted of a ceramic disk obtained from Mound—E.G.&G., Miamisburg, Ohio, which is a nominal 94% by weight alumina ceramic body designated as "94ND2." The ceramic disks were formed from the starting materials and relative proportions indicated by Table 1.

TABLE 1

| $(Al_2O_3)$ | Alumina | 93.26 |
| $(Mg(OH)_2)$ | magnesium hydroxide | 1.62 |
| $(CaCO_3)$ | calcium carbonate | 0.66 |
| $(SiO_2)$ | Silica | 4.46 |

A ceramic powder of the composition in Table 1 was prepared by wet milling these components. After drying, the powders were calcined in air to yield the final ceramic powder composition. The calcined ceramic powder was isostatically molded to a maximum pressure of about 30,000 psig yielding a preformed disk.

The preformed disk was then provided with two cermet pass-throughs or conductors therethrough. The preformed disk was counter bored to yield two holes spaced from each other with centers thereof preferably falling on the diameter of the disk and preferably spaced from the perimeter of the disk at a distance of about one-half the radius of the disk. Excess powder was removed and edge protrusions smoothed as necessary. The disk was then sintered in wet hydrogen (dew point of about 40° C.) at about 1,600° C. for about 3 hours and wet hydrogen flow rate of about 30 SCFH. The ceramic density was at least about 3.75 gm/cc.

A cermet powder composition was prepared from the following starting materials and relative proportions: 50% by weight of alumina powder and 50% by weight of molybdenum metal powder (325 mesh). These materials were milled overnight in a ball mill jar to achieve a preliminary dry blend without agglomeration. A slurry of the cermet powder was then prepared by placing about 20 grams of the cermet mixture in a cup and adding thereto about 9 ml of butyl carbitol acetate and about 4 drops of Nuosperse #657 surfactant (from Tenneco Chemical Co.). The mixture was stirred for a minimum of 15 minutes in a rotator until the slurry was creamy.

The holes in the disk were then filled with the slurry using an eyedropper while a vacuum was being pulled through the holes of the disk. A piece of filter paper was positioned between the disk holder of the vacuum pump and the disk. Additionally, when filling the first hole of the disk, the other hole was covered with filter paper to allow the vacuum pump to pull an adequate vacuum through the uncovered hole so as to uniformly fill the hole with the slurry and avoid the formation of voids within the cermet conductors. The slurry was applied to each hole leaving a small amount of excess over the top of each hole. The disks were then turned over (excess lump facing downward) on a drying tray and placed in an oven to dry overnight at about 130° C. and then allowed to cool to about room temperature. The surfaces of the disks were then ground to a uniform, flat surface. The disk was then sintered in a wet 95%/argon 5% hydrogen environment (dew point from about +20° C. to about −10° C.) at about 1,500° C. for 45 minutes. The wet argon/hydrogen was supplied at a flow rate of about 4.5 SCFH. The thus formed disk has two cermet conductor exposed portions on each of the opposing surfaces of the disk.

Two of the exposed portions of cermet on one of these opposing surfaces of the disk were metallized and brazed with copper to form the indicator contact zone (28) and the reference contact zone (50) of the respective indicator electrode (20) and reference electrode (40) to which lead wires (86) and (88) may be soldered.

EXAMPLE 2

Indicator Electrode

Utilizing direct RF reactive sputtering, iridium dioxide ($IrO_2$) was sputtered onto one of the exposed portions (24) of the first cermet conductor (22) so as to entirely cover this exposed portion (24). Prior to sputtering, the exposed portion (24) had been plasma cleaned. Iridium was sputtered from a pure (99.995%) iridium, 7.62 cm (3-inch) diameter planer source (target). A 13.5 megahertz RF power supply capable of 500 watts was used to drive the source. The sputtering pressure was maintained using a servo driven leak valve and automatic pressure controller closed loop network. A chamber pressure of about $1 \times 10^{-2}$ torr (1.33 Pa) was maintained with an oxygen flow rate of about 6.0 standard cubic centimeters per second. A nominal power density of about 5.5 watts/cm$^2$ was maintained with a net reflected power of less than about 0.055 watts/cm$^2$ for the deposition cycles. A pre-sputter of the source was done with argon and oxygen to clean the source. A source to substrate (exposed portion (24)) distance of 3.25 cm was used. Substrate (ceramic/cermet disk) was mounted in direct contact with a chill block maintained at a temperature of about 18° C. to about 20° C. by water cooling. The thickness of the deposited $IrO_2$ coating (24) was about 9340 angstroms.

The $IrO_2$ coating (26) was then coated with a perfluorocarbon copolymer coating (30) by spin-coating the indicator electrode (20) once with a 10 wt % solution of Nafion® 117 perfluorocarbon copolymer, which has an equivalent weight of about 1100, in a mixture of lower aliphatic alcohols and water at about 3000 rpm for about 30 seconds and air dried at about 130° C. The solution was purchased as a 5 wt. percent solution from C. G. Processing, Inc. now Solution Technologies, Inc., Mendenhall, Pa. and concentrated to 10 wt. percent by evaporation. The indicator electrode was placed in a room temperature oven and the oven temperature was slowly brought up to 210° C. over a period of about 45 minutes. The electrodes were annealed at 210° C. for thirty minutes in the oven. The electrode was slowly cooled to room temperature over a period of about 1 hour by turning off the oven and leaving the electrode in it while cooling. The electrode was placed in a pH phosphate buffer solution (0.1M) and heated to boiling and boiled for thirty minutes. The buffer solution containing the electrode was removed from heat and allowed to cool. The electrode was stored in the solution.

The electrode was tested using cyclic voltammetry (CV) in the presence of ferricyanide, and the reversible CV for the reduction of ferricyanide to ferrocyanide was effectively eliminated as an interference by the annealed perfluorocarbon copolymer coating, i.e., migration of the $Fe(CN)_6^{-4}$ anion to the electrode $IrO_2$ coating was prevented.

Testing of the indicator electrode (20) prior to coating with the perfluorocarbon copolymer indicates that it does not experience the "aging" effects that plague iridium dioxide/titanium wire electrodes. Sputtered iridium dioxide onto titanium wire electrodes stabilize after about 30 hours of hydration in 0.1M phosphate buffer after boiling 30 minutes in deionized water. On the contrary, the iridium dioxide/cermet indicator electrode (20) embodying the present invention stabilizes in a matter of minutes after boiling in deionized water. In fact, periodic standardization tests in the phosphate buffer showed no significant change in the standardization curve with time over a 70-day period. The same is true when standardization tests were performed in a "universal buffer" (0.01M phosphate 0.01M borate, 0.01M acetate and 0.1M potassium nitrate) over a 70-day period. See FIG. 6.

EXAMPLE 3 pH Response of $IrO_2$/Cermet Indicator Electrodes

In this example, indicator electrodes were prepared according to Example 2 using three ceramic/cermet disks as prepared in Example 1, except the $IrO_2$ sputtering depositions were run at 250 watts net power for ten minutes (no bias or presputter etching was employed). Hydrogen firing was employed prior to sputtering to reduce the molybdenum oxide surface to molybdenum. The $IrO_2$ layer thickness of each electrode was about 7500 Angstroms.

The electrodes were tested for pH responses in "universal" buffer as well as sixteen NBS primary and secondary standard buffers (available from NBS, Gaithersburg, Md. ranging from pH 1.1 to 12.6. A typical pH response curve (potential vs. time after a step change in pH) is shown in FIG. 7. A Nernst plot (pH vs. potential) is shown in FIG. 8. Table 2 tabulates pH response data, i.e., the slope, intercept and goodness number of fit of the Nernst plot, for each of the indicator electrode prepared.

TABLE 2

| | pH Response of $IrO_2$/CERMET Electrodes | | | |
|---|---|---|---|---|
| Ceramic/ Cermet Disk | Indicator Electrode | Slope (mV/pH) | Intercept (mV vs. Ag/AgCl) | Goodness of Fit Statistic |
| A | 1 | −51.2 | 217.7 | 98.6 |
|   | 2 | −52.5 | 202.2 |   |
| B | 1 | −52.7 | 230.8 | 97.9 |
| C | 1 | −49.7 | 207.8 | 98.6 |
|   | 2 | −52.9 | 211.6 |   |

It was interesting to note that the indicator electrodes shown in Table 2 show slopes consistently lower than the theoretical −59 mV/pH unit expected from the Nernst equation. This was in contrast with $IrO_2$ sputter coated titanium wire electrodes which consistently exhibited slopes averaging −59 mV/pH unit. This sub-Nernstian behavior was due to exposed molybdenum in pits or recesses in the $IrO_2$ surface. SEM data on uncoated cermet conductor surfaces showed a high degree of heterogeneity, with grain sizes of molyhdbenum and aluminum approaching 5 microns. SEM results on thin Ir coated cermets (about 200 Angstroms thick Ir layer) showed preferential sputtering of the iridium to the alumina (no iridium was found on the molybdenum crystals). SEM data on $IrO_2$ (about 5000 Angstroms thick)/titanium (Ti, about 400 Angstroms thick)/Cermet indicator electrodes revealed large pits which EDX analysis showed to contain molybdenum and aluminum and only small amounts of Ti or Ir.

A number of avenues exist for circumventing the molybdenum exposure problem. These include changing the cermet metal to one more compatible with the specific metal oxide of the indicator electrode, such as chromium or titanium for iridium oxide; reduction in grain size of the cermet yielding a more homogeneous surface; utilizing a sputtered sublayer of a metal more compatible to molybdenum and chemically more inert (i.e., gold (Au)); metallization of the cermet surface prior to sputtering; or a combination of the foregoing.

EXAMPLE 4

$IrO_2$/Au/Cermet Indicator Electrode

In this example, the surface of a cermet conductor of a ceramic/cermet disk (header) prepared according to Example 1, was coated with a gold (Au) barrier layer to isolate the molybdenum (Mo) from the subsequent iridium oxide coating. The procedure employed a pre-sputtering of about 2000 Angstroms of Au over the surface of the cermet conductor. A registered mask was utilized which would also result in the coating of the edge of the cermet conductor surface. The Au sputtered cermets were then electroplated about 4 to 8 microns of Au to fill in the voids in the cermet conductor surface. The cermet conductor surface was then polished with alumina, plated a second time with Au in similar fashion, and repolished. Cyclic voltammetry revealed no Mo oxidation in 0.5M sulfuric acid. Cyclic voltammetry of a Au sputtered cermet conductor (sputter coating of about 2000 Angstroms of Au) without the electroplated Au coating did not isolate the Mo from the test solution.

The Au plated cermet conductors were then sputter coated with about 2000 Angstroms of $IrO_2$ using reactive RF sputtering. FIG. 9 shows the pH response for an $IrO_2$ coated/polished Au barrier layer/cermet indicator electrode in a universal buffer. The electrode responded with a slope of $-60.38$ mV/pH unit with an intercept of 741.33 mV (vs. Ag/AgCl), and a goodness of fit statistic of 99.99. The average response time to pH changes was about 0.31 minutes over the pH range of 2.4 to 11.4. The pH matched that obtained by a glass electrode to within plus or minus 0.02 pH.

After the above test, the $IrO_2$ layer was still intact; however, upon standing overnight in a buffer solution, the $IrO_2$ was found to spall from the surface. All electrodes prepared in this fashion (i.e., direct RF sputtering of $IrO_2$ onto Au) eventually showed spalling of $IrO_2$ from the Au upon standing in a buffer solution. Titrations run before the spalling of the $IrO_2$ coatings gave a Nernstian response. To improve the adhesion of the $IrO_2$ layer to the Au plated cermet conductor, a thin layer of Ti (between the Au and $IrO_2$) may be used as an adhesion layer. The $IrO_2$ adheres exceptionally well to Ti in buffer solutions. Additionally, sputtered Au adheres well to Ti.

EXAMPLE 5

$IrO_2$/Ti/Au/Cermet Indicator Electrode a. Ceramic Substrate and Cermet Conductors The ceramic substrate consisted of a ceramic disk (header) obtained from R and W Products, Inc., Auburn, Calif., which is a nominal 93% by weight alumina ceramic body designated "R and W 93." The ceramic density was at least about 3.69 gm/cc. This ceramic substrate is similar to that of Example 1.

The cermet powder composition was prepared from the following starting materials and relative proportions: 46% by weight alumina powder, 49% by weight of molybdenum (Mo) powder (325 mesh), and 5% other inert materials. The ceramic/cermet headers contained 2 or 3 cermet conductors (pins) equispaced from each other about the center of the header. The exposed portions of the cermet conductors on the surface of the header which will face the interior of the housing (284) were metallized and brazed with copper. The brazing compound was a Ag/Cu alloy known as "Cusil" available from GTE Products Corp., Stamford, Conn. The header was then silver soldered to the housing (284) as shown in FIG. 4.

A snap-on connector (294) of an insulating material, such as PVC, in the form shown in FIG. 5, had a "Pogo" pin (308) corresponding to each electrode on the ceramic/cermet header. "Pogo" pins (308) are available from Augat-Pylon, Attleboro, Mass. The "Pogo" pins have spring-loaded pins within a sleeve. The pins are urged toward their corresponding contact zone on the header (10) for making electrical contact therewith. The sleeve (310) of the "Pogo" pin (308) was secured within a socket (298) of the snap-on connector (294). The electrical connections to the pH sensing equipment were made to the pin opposite the portion of the pin making contact with the contact zone.

b. $IrO_2$/Ti/Au Coating

A header having three cermet conductors was used. Two of the three cermet conductor surfaces on the side opposite the interior of the housing (284) were coated with gold by first sputtering and then electroplating gold according to Example 4. A "two" dot registered mark, which had larger diameters than the "three" dot registered mark used for the gold coating, was employed to RF sputter about 2000 Angstroms of Ti followed by about 2000 Angstroms of $IrO_2$. On the two cermet conductor surfaces coated in this manner, no Au coating was exposed by carefully aligning the "two" dot registered mark. The third Au coated cermet conductor surface was not coated and may be subsequently coated with, for example, Ag and anodized to form a Ag/AgCl reference electrode.

After initially boiling the header in DI water for 30 minutes to hydrate the $IrO_2$, two titrations were performed on these indicator electrodes. A Nernstian response was obtained (slope$=-59.9$ mV/pH unit), with hysteresis error improving from about plus/minus 0.1 pH units to about plus/minus 0.05 pH units from the first titration to the second titration. FIG. 10 is a Nernst plot comparing the pH response of the $IrO_2$/Ti/Au/Cermet indicator electrode to a glass electrode.

The Ti sublayer substantially improved the $IrO_2$ adhesion over that observed with no Ti layer. Additionally, the Ti sublayer did not appear to introduce any additional hysteresis when compared to IrO$_2$ on alumina ceramic.

EXAMPLE 6

IrO$_2$/Ir/Ti/Au/Ti/Cermet Indicator Electrode a. Sample Preparation

The edge of a three electrode ceramic/cermet header having three (3) cermet conductors (pins) embedded in a ceramic substrate adjacent to the surface was tapered on a lathe to allow for improved sanding and polishing of the surface. The header was sanded with 1200 (European) grit silicon carbide paper on a lapping wheel for about 5 minutes. The cermet header was then sonicated in a 20:1 soap/water solution (Buehler Ultramet Sonic Cleaning Solution) for about three minutes, rinsed with acetone (A.C.S. Certified), sonicated in methylene chloride (A.C.S. Certified) for about three minutes, and dried with nitrogen. The cermet header was then diamond polished (lapped) using, in succession, 6 micron, 1 micron, and 0.25 micron diamond paste (Buehler). The cermet was rinsed with deionized (DI) water, sonicated in a cleaning solution (see above) for about three minutes, rinsed with acetone (A.C.S. Certified), sonicated in methylene chloride (A.C.S. Certified) for about three minutes and dried with nitrogen after each diamond paste lap.

b. DC Magnetron Sputter Coating Phase I: Ti/Au

The cermet header was placed into a stainless steel holder and covered by a registered mask that exposed one of the surfaces of each of the three cermet pins contained in the header. The mask assembly was then placed on a water cooled etching station in the vacuum chamber of a Leybold Heraus Z400 DC magnetron sputtering system, Leybold Heraus Technologies, Inc., Enfield, Conn., and evacuated to a base pressure of less than about $8 \times 10^{-6}$ mbar. The titanium target was pre-sputtered for about 2.5 minutes to remove any titanium oxide coating. About 1000 Angstroms of titanium was then sputtered onto the exposed surface of the cermet pins in argon at a pressure of about $1.1 \times 10^{-2}$ mbar at about 100 W. The sputtering rate was about 3 Angstroms/second as measured by a Leybold Heraus XTC quartz crystal monitor. About 5000 Angstroms of gold was then sputtered onto the titanium coated pins at a pressure of about $3 \times 10^{-3}$ mbar at about 55 W. The deposition rate was determined to be about 15 Angstroms/second. The titanium layer is preferably present to improve the adhesion of the gold layer to the cermet pins. Therefore, the titanium layer is called an adhesion layer. It is noted that a layer of gold directly sputtered onto the cermet may not always adhere thereto after boil testing (boiling for 30 minutes in DI water).

c. Electroplated Au Coating

The cermet header was set up so that three spring-loaded electrodes ("pogo" pins) made electrical contact with the backsides of the cermets from inside the stainless steel housing (see FIG. 5). The pogo pins and the outside of the housing were wired so that the entire assembly constituted the cathode. Gold plating was performed at 60° C. in a gold cyanide plating bath containing about 1 troy oz. per gallon of electroplating solution ("Orotemp 24" solution available from Technic, Inc. of Providence, R.I.) equipped with a platinum anode. The exposed surface of the coated cermet pins were plated for one hour at a constant current density of about 3.2 mA/cm$^2$. The thickness of the gold layer was calculated to be about 7.5 microns. After plating, the cermet was rinsed in DI water, boiled 30 minutes in DI water, sonicated for 10 minutes in DI water, and dried at about 120° C. for at least 1 hour.

This gold coating fills in the voids on the surface of the cermet pin (which can be as large as 2 to 3 microns) and serves as a barrier layer to corrosion of the underlying molybdenum metal contained in the cermet pin by IrO$_2$ or the electrolyte. Direct sputtering of about 5 microns of gold did not result in the formation of a barrier layer, since sputtering is essentially a line-of-right process, whereas plating proceeds in two dimensions.

d. DC Magnetron Sputtering Phase II: Au/Ti/Ir/IrO$_2$

After drying, the header was placed back into the mask assembly and covered by a registered mask with slightly larger holes, exposing two of the three Au coated cermet pins. The Au plate thereon was sputtered with an additional 5000 Angstroms of Au followed by about 1000 Angstroms of titanium (the deposition procedure for Au and Ti was identical to that described in Phase I above). Next, about 2000 Angstroms of iridium was deposited in argon at a pressure of about $4.5 \times 10^{-2}$ mbar at about 90 W. The iridium deposition rate was determined to be about 7.5 Angstroms/second. Finally, about 2000 Angstroms of iridium oxide was deposited thereon by reactively sputtering iridium in a pure oxygen plasma at a pressure of about $5.0 \times 10^{-3}$ mbar at about 160 W. The sputtering rate of the iridium oxide was measured to be about 44 Angstroms/second. After coating with iridium oxide, the chamber was vented with nitrogen and the cermet header removed and stored in a desiccator.

This titanium layer also acts an adhesion layer to improve the adhesion of the sputtered iridium onto the gold layer. The iridium layer prevents oxidation of the titanium layer by the IrO$_2$ and helps maintain the long term accuracy of the pH electrode since iridium oxidizes to IrO$_2$ and the IrO$_2$ which provided the driving force this oxidation is reduced to iridium. For this reason, it is preferred to have a metal underlayer below the metal oxide layer wherein the metal in the metal underlayer and the metal oxide layer are the same metal.

e. pH Response of IrO$_2$ on Ceramic/Cermet

FIGS. 11 and 13 show the pH response of the electrode as incremental additions of 10N NaOH were added to "Universal Buffer" (0.1M H$_3$PO$_4$ 0.1M HAc, 0.1M H$_3$BO$_3$ and 0.1M KNO$_3$).

FIG. 11. pH 2.5 to 5.18.
FIG. 12. pH 5.44 to 8.78.
FIG. 13. pH 8.95 to 11.72.

FIGS. 14 through 16 show the pH response of the electrode as the above solution is "back" titrated to pH 2.39 with concentrated H$_3$PO$_4$.

FIG. 14. pH 11.53 to 7.56
FIG. 15. pH 7.33 to 4.96
FIG. 16. pH 4.68 to 2.39

The "Nernst" plot (mV vs. pH) is shown in FIG. 17 which shows the expected Nernstian behavior for IrO$_2$.

EXAMPLE 7

Iridium Oxide Coated on Hastelloy C/S-Glass a. Sample Preparation

S-glass headers containing three Hastelloy C-276 pins were obtained from EG&G Mound Laboratories, Miamisburg, Ohio. S-glass is an injection moldable glass ceramic manufactured by Schott Optical Glass, Inc. of Durayea, PA. and sold under the designation of "35-S". S-glass is a composite containing lithium oxide (10.9 to 13.7% by weight), potassium oxide (3.78 to 4.01% w), alumina (4.38 to 5.13% w), boron oxide (1.1 to 1.49% w), tantalum oxide (2.14 to 2.76% w) with the balance being silica. Sample preparation was the same as described in Example 6 for the ceramic/cermet headers thereof.

b. DC Magnetron Sputter Coating Phase I: Ti/Au

The S-glass header was covered with a registered mask which exposed a surface of one of the Hastelloy pins. The pin was coated with about 1000 Angstroms of titanium followed by about 5000 Angstroms of Au as described in Example 6.

c. Electroplated Au Coating

About 7.5 microns of Au was deposited on the coated Hastelloy pin using the same conditions as in Example 6. As before, the gold coating acts as a barrier layer to prevent the oxidation of the Hastelloy by $IrO_2$.

d. DC Magnetron Sputtering Phase II: Au/Ti/Ir/IrO$_2$

The plated pin was then coated with about 5000 Angstroms Au, then about 1000 Angstroms Ti, then about 2000 Angstroms Ir, and finally about 2000 Angstroms $IrO_2$ using the same conditions as reported in Example 6.

e. pH Response of IrO$_2$/Ti/Au/Ti/Hastelloy pin in S-glass Indicator Electrode The pH response was measured in universal buffer according to the procedure described in Example 6 above:

FIG. 18. pH 2.33 to 4.30
FIG. 19. pH 4.61 to 8.89
FIG. 20. pH 9.07 to 11.71
FIG. 21. pH 11.38 to 8.42
FIG. 22. pH 8.30 to 5.96
FIG. 23. pH 5.36 to 2.32

The Nernst curve for the S-glass electrode is shown in FIG. 24, which shows the expected Nernstian behavior for $IrO_2$.

EXAMPLE 8

Effect of Annealed Perfluorocarbon Copolymer Coating on Indicator Electrode

In this example, two indicator electrodes according to the present invention were prepared. The first indicator electrode was prepared according to the procedure of Example 2. The second indicator electrode was prepared in similar fashion with the exception that the annealed perfluorocarbon copolymer coating was not used. These two indicator electrodes were tested for interference by redox species. The annealed perfluorocarbon copolymer coated indicator electrode produced a Nernst plot whose slope in NBS buffers (available from NBS, Gaithersburg, Md.) was essentially unaffected on addition of ferricyanide to the buffer solutions (slope went from −47.6 to −47.3 mV/pH unit), while that of the uncoated electrode decreased sharply to −7.3 mV/pH unit indicating that the annealed polymer coating effectively blocks redox interference. Therefore, where such redox interferences are expected to be encountered, the annealed polymer coating is preferably utilized.

EXAMPLE 9

AgCl/Ag/Au/Cermet Reference Electrode

In this example, a AgCl/Ag/Au/Cermet reference electrode was prepared. The surfaces of the cermet conductors on one side of a ceramic/cermet header prepared according to Example 1 were coated with gold (Au) using RF sputtering and electroplating according to Example 4. One of the gold coated cermet conductors (to be the reference electrode) was then sputter coated with about 2000 Angstroms of silver (Ag), such that the Au layer was entirely covered by the Ag coating. In the case of silver, direct electroplating of silver onto the 50% w molybdenum metal cermet exposed surface (portion (44)) produced silver dendrites rather than a smooth, uniform plate.

The reference electrode with the silver coating was then immersed in a 0.1M aqueous potassium chloride solution (acidified with HCl) adjacent a platinum screen. The silver coated electrode was then anodized to form a AgCl layer on the silver surface to produce the desired Ag/AgCl coating (46) of the reference electrode (40). Current flowing between the silver-coated electrode (anode) and the platinum screen (cathode) was adjusted to maintain about 4 milliamperes per square centimeter of the silver coating surface for about 30 seconds. The reference electrode (40) was then removed from the potassium chloride solution and washed with water, dried with nitrogen, and dried at about 120° C. overnight.

The AgCl/Ag/Au/cermet reference electrode yielded a stable electrode potential after anodization in potassium chloride once the silver chloride outer layer was formed on the silver coating and also when stored in saturated KCl.

The reference electrode silver/silver chloride coating was then coated with an immobilized electrolyte coating, in this example, a partially quaternized halogenated polymer.

The partially quaternized polymer was prepared as follows. About 0.1 mole of polyvinylbenzylchloride purchased from Aldrich Chemical Co., Milwaukee, Wisc. of molecular weight of about 50,000 to about 100,000 daltons, was dissolved in THF with about 0.24 moles of triethyl amine and refluxed for one hour. A white polymeric material precipitated. The precipitate was washed and extracted with THF yielding a white polymeric crystalline substance which was soluble in 2-methoxyethanol, and formed a slurry in 1,1,1,3,3,3,-hexafluoro-2-propanol, and insoluble in water. Infrared analysis indicated partial quaternization of the polymer. Elemental analysis of the polymer indicated about 33% quaternization.

The silver/silver chloride (Ag/AgCl) coated reference electrode was spray-coated with a 2.5 weight percent solution of the partially quaternized polymer in 2-methoxy ethanol. The electrode was then dried for about 1 hour at about 100° C. Alternatively, the quaternized polymer may be applied by screen-printing or any other suitable manner.

The dry electrode was spin-coated two times with a 10 wt percent Nafion ® 117 perfluorocarbon copolymer, which has an equivalent weight of about 1100, in a solution of lower aliphatic alcohols and water and annealed according to the procedure described in Example 2. After hydration in DI water, the response of this reference electrode to pH was determined in universal buffer. The results, plotted in FIG. 25, show negligible variation of potential with pH.

EXAMPLE 10

Completely Quaternized Polymer

About 0.1 mole of the polyvinyl benzylchloride (poly(chloromethyl)styrene) described in Example 9 was dissolved in 100 ml methoxyethanol. About 0.5 moles of triethylamine was added and the solution heated at about 60° C. for about an hour. The solution was stirred at ambient temperature for 2 days. The polymer was precipitated by adding about 100 ml of methoxyethanol and about 200 ml THF. The precipitate was washed with THF and dried. The product was soluble in water, methoxy ethanol and methanol. Infrared analysis indicated complete quaternization of the polymer.

EXAMPLE 11

Silver/Silver Chloride Coated On a Ceramic/Cermet a. Electroplated Ag Coating

In Example 6, the remaining cermet pin which does not have an Ir/IrO$_2$ coating would be electroplated with silver. This would be accomplished by setting up the ceramic/cermet header so that the three spring-loaded electrodes ("pogo" pins) are making electrical contact with the backsides of the cermet pins from inside a stainless steel housing (see FIG. 5). The pogo pin in electrical contact with the remaining cermet pin is wired so that this pin constitutes the cathode. Silver plating is performed in a silver non-cyanide plating bath containing about 3 oz. Ag per gallon of plating solution equipped with a platinum anode. The exposed surface of the coated cermet pin is plated for about 30 minutes at a constant current density of about 5.4 mA/cm$^2$ to yield a silver plating about 9 Angstroms thick.

b. Anodization of Ag

The silver layer would then be anodized in a 1M KCl acidic solution at a constant current density of about 4 mA/cm$^2$ for about two minutes, to form a silver/silver chloride electrode. The ceramic/cermet header would then be rinsed in DI waste and dried with nitrogen.

c. Quaternized Polymer Application

A quaternized poly(chloromethyl)styrene coating would then be applied to the silver/silver chloride (Ag/AgCl) electrode so as to completely cover same. The quaternized poly(chloromethyl)styrene may be partially or completely quaternized with completely quaternized being preferred. The coating may be applied by any suitable method, for example, applying the coating with an air brush using methooxyethanol as the solvent. Example of suitable polymer/solvent solution are a 2% solution of completely quaternized trimethylamine poly(chloromethyl)styrene and an 8.6% solution of partially quaternized (about 30% quaternized) triethylamine poly (chloromethyl) styrene. The coating is then air dried for about 30 minutes and placed into an oven at about 130° C. for about 1 hour. After cooling to room temperature, the ceramic/cermet header electrodes, i.e, the indicator and reference electrodes, are coated with the perfluorocarbon copolymer and annealed in the manner of Example 6. The response of the Ag/AgCl electrode to chloride ions present in the environment of interest is expected to be minimal.

The procedure of this Example 11 is also applicable to the remaining Hastelloy C pin of the Hastelloy C/S-glass header of Example 7.

d. Perfluorocarbon Copolymer Coating and Annealing

Prior to the anodization of the Ag on the reference electrode, the IrO$_2$ on the indicator electrodes would be hydrated by boiling in DI water for about 30 minutes and then dried.

After the application and drying of the quaternized polymer coating of the reference electrode, the indicator and reference electrodes are preferably coated with an annealed perfluorocarbon copolymer. Preferably, the surface of the ceramic/cermet header having the indicator and reference electrodes is coated, such as by spin-coating with a 10% by weight Nafion ® 117, perfluorocarbon copolymer, which has an equivalent weight of about 1100, in a mixture of lower aliphatic alcohols and water. Such a solution is commercially available from Solution Technologies, Inc., Mendenhall, Pa. The ceramic/cermet header is spin-coated with this solution, for example, at about 3000 rpm for about 100 seconds. The coating is then air dried for about 15 minutes at about 130° C. to flash dry the first application of the solution. This flash drying of the Nafion ® coating inhibits the dissolution of the quaternized polymer coating and mixing of the two polymers. The Nafion ® coating is then annealed at about 210° C. for about 30 minutes. The perfluorocarbon copolymer coating procedure is preferably repeated at least once more, preferably flash drying and annealing after each application to inhibit the dissolution of the previously annealed layer of Nafion ® copolymer.

After the ceramic/cermet header cools to about room temperature, the annealed Nafion ® coating, the quaternized polymer coating and the IrO$_2$ layer are hydrated, preferably by placing the ceramic/cermet header in DI water at about 50° C. for about 1.5 hours and then air dried.

The foregoing procedure will produce a solid state pH sensor having both an indicator electrode and a reference electrode on a single ceramic/cermet header. The respective electrodes may then be electrically attached to pH sensing equipment by any suitable means such as by using "pogo" pins as shown in FIG. 5.

Alternatively, individual indicator electrodes or reference electrodes may be produced on separate ceramic/cermet headers and used in combination with each other or in conjunction with other indicator or reference electrodes.

EXAMPLE 12

Metal oxide pH Electrode and Associated Transduction Electronics

In this example, an indicator electrode (a titanium wire with IrO$_2$ RF sputtered thereon) was utilized with a digital multimeter as opposed to a standard pH meter as in the previous Examples hereto. The digital multimeter system as shown in FIG. 26 was employed to test the effect of amplifier impedance on the drift of an IrO$_2$ pH indicator electrode. The bias current, or the current passed through a pH sensor, is a function of the electromotive force (EMF) generated by the sensing system and the input impedance of the transducer used to amplify the sensor millivolt signal. The higher the impedance of the electronic circuitry, the lower the bias current.

As shown in FIG. 26, the system had the indicator electrode (400) and a standard reference electrode (Ag/AgCl) (402), which form a pH sensor, connected to a high impedance (FET) differential amplifier circuit (404). The output of the circuit (404) was fed to a voltage to current converter (406), then to a digital controller (408) and finally to a pH read-out device (410). The circuit (404) was a combination of two operational amplifiers (412) and (414) together with the resistors (416) (9K resistor), (418) (1K resistor), (420) (1K resistor) and (422) (9K resistor) and a variable resistor (424) (10K variable resistor), as shown in FIG. 27. The operational amplifiers used were Model OPA104BM available from Burr-Brown Research Corp., Tucson, Ariz. The converter (406) used was a Model 160T ACROMAG® transmitter (available from Acromag, Wixon, Mich.) which converted the sensor millivolt signal to a current signal (4-20 mA) compatible with a Model CL6242 PROVOX® controller (available from Fisher Controls International, Inc., Marshalltown, Ia.), the digital controller (408) used. The ACROMAG® transmitter (406) used without the circuit (404) had an input impedance of about 5 megaohms and a bias current of about 26 nanoamperes (nA) as measured by an electrometer when the sensor was immersed in a pH 4.01 phosphate buffer. Attaching the circuit (404) to the front end of the ACROMAG® transmitter (406) using teflon 8-pin connectors (426) as shown in FIG. 26 reduced the bias current to about 8 picoamperes (pA). The circuit (404) provided an input impedance of about $10^9$ megaohms as compared to about 100 megaohms impedance for a digital multimeter (without circuit (404)). The impedance provided by circuit (404) is comparable to that of high impedance pH meters designed for high impedance glass electrodes.

FIG. 28 provides a comparison of the foregoing system with (Line A) and without (Line B) the circuit (404) and shows the effect of bias current on the drift of the sensor. Without the circuit (404), drift of electrode potential would likely be unacceptable (drift of about 2.8 pH units/8 days); whereas, with the circuit (404), performance was dramatically improved (drift of about 0.2 pH units/8 days).

Additionally, it was observed that the pH response of the electrode without the circuit (404) was sub-Nernstian (slopes of about $-53$ to about $-55$ mV/pH unit); whereas, with the circuit (404), the electrode exhibited a constant Nernstian response (slopes of about $-61.7$ to about $-61.4$ mV/pH unit).

Not wishing to be bound to any particular theory, the drift of the electrode potential may be explained as follows. The potential of the electrode, at equilibrium, is obtained by applying the Nernst equation to the following half-cell reaction:

$$2 IrO_2 + 2e + 2H^+ = Ir_2O_3 + H_2O \quad \text{Half-cell Reaction}$$

$$E = E^\circ - \frac{RT}{2F} \ln \frac{(Ir_2O_3)(H_2O)}{(IrO_2)(H^+)^2} \quad \text{Nernst Equation}$$

-continued $$E = E^\circ - 0.029 \log \frac{(Ir_2O_3)}{(IrO_2)} - 0.059 \text{ pH}$$

As the net current is passed, the ratio $(Ir_2O_3)/(IrO_2)$ changes due to the oxidation or reduction, depending upon the sign of the bias current. For a small bias current in the pA range, the effect is minimal as shown above. For larger bias currents (nA range), the effect is dramatic and a large pH error results. Further, the thinner the iridium oxide coating, the more sensitive its potential to the current draw.

Since metal oxide pH electrodes, such as $IrO_2$, are excellent electronic conductors (conductivity of about $10^4 \text{ohm}^{-1}\text{cm}^{-1}$), it is normally assumed that low impedance preamplifiers may be employed when using pH sensors employing such electrodes without introducing any error in the measurement. On the contrary, as the foregoing results demonstrate, high impedance preamplifier circuitry was required to obtain an accurate, stable pH measurement. This is believed to be the result of drawing current through the thin layer of metal oxide which causes the oxidation state, and thus the potential of the metal oxide pH electrode, to change. Thus, the input impedance of the measuring device used is preferably at least about $10^6$ megaohms.

Such circuitry or equivalent thereof is preferably employed to provide the high impedance required when utilizing an indicator electrode of the present invention in a pH sensor with a digital multimeter and may be placed inside the housing (84) or (284), for example.

It will be apparent from the foregoing that many other variations and modifications may be made in the apparatus and methods herein before described, by those having experience in this technology, without departing from the concept of the present invention. Accordingly, it should be clearly understood that the apparatus and methods depicted in the accompanying drawings and referred to in the foregoing description are illustrative only and not intended to have limitations on the scope of the invention.

What is claimed is:

1. A solid state pH sensor for pH sensing equipment, said pH sensor comprising:
   (a) an indicator electrode, said indicator electrode comprising
      (1) a first electrically conductive conductor imbedded in a first electrically non-conductive substrate, said first electrically conductive conductor having a first electrically conductive conductor exposed portion,
      (2) a metal/metal oxide coating on said first electrically conductive conductor exposed portion, such that said metal/metal oxide coating entirely covers said first electrically conductive conductor exposed portion,
      (3) a first annealed perfluorocarbon copolymer coating on said metal/metal oxide coating, such that said first annealed perfluorocarbon copolymer coating entirely covers said metal/metal oxide coating, and
      (4) an indicator contact zone electrically connected to said first electrically conductive conductor, wherein said indicator contact zone is utilized in making electrical contact between said first electrically conductive conductor and said pH sensing equipment; and (b) a reference electrode, said reference electrode comprising
  (1) a second electrically conductive conductor imbedded in a second electrically non-conductive substrate, said second electrically conductive conductor having a second electrically conductive conductor exposed portion,
  (2) a metal/metal salt coating on said second electrically conductive conductor exposed portion, such that said metal/metal salt coating entirely covers said second electrically conductive conductor exposed portion,
  (3) an immobilized electrolyte coating on said metal/metal salt coating, such that said immobilized electrolyte coating entirely covers said metal/metal salt coating,
  (4) a second annealed perfluorocarbon copolymer coating on said immobilized electrolyte coating, such that said second annealed perfluorocarbon copolymer coating entirely covers said immobilized electrolyte coating, and
  (5) a reference contact zone electrically connected to said second electrically conductive conductor, wherein said reference contact zone is utilized in making electrical contact between said second electrically conductive conductor and said pH sensing equipment;

(c) wherein said indicator and reference electrodes are electrically insulated from each other.

2. The solid state pH sensor of claim 1 having a first barrier layer of a noble metal between said first electrically conductive conductor exposed portion and said metal/metal oxide coating, such that said first barrier layer entirely covers said first electrically conductive conductor exposed portion and said metal/metal oxide coating entirely covers said first barrier layer, and a second barrier layer of noble metal between said second electrically conductive conductor exposed portion and said metal/metal salt coating, such that said second barrier layer entirely covers said second electrically conductive conductor exposed portion and said metal/metal salt coating entirely covers said second barrier layer.

3. A solid state pH sensor for pH sensing equipment, said pH sensor comprising:

(a) an indicator electrode, said indicator electrode comprising
  (1) a first electrically conductive conductor imbedded in a first portion of an electrically non-conductive substrate, said first electrically conductive conductor having a first electrically conductive conductor exposed portion,
  (2) a metal/metal oxide coating on said first electrically conductive conductor exposed portion, such that said metal/metal oxide coating entirely covers said first electrically conductive conductor exposed portion,
  (3) an annealed perfluorocarbon copolymer coating on said metal/metal oxide coating, such that said annealed perfluorocarbon copolymer coating entirely covers said metal/metal oxide coating, and
  (4) an indicator contact zone electrically connected to said first electrically conductive conductor, wherein said indicator contact zone is utilized in making electrical contact between said first electrically conductive conductor and said pH sensing equipment; and (b) a reference electrode, said reference electrode comprising
  (1) a second electrically conductive conductor imbedded in a second portion of said electrically non-conductive substrate, said second electrically conductive conductor having a second electrically conductive conductor exposed portion,
  (2) a metal/metal salt coating on said second electrically conductive conductor exposed portion, such that said metal/metal salt coating entirely covers said second electrically conductive conductor exposed portion,
  (3) an immobilized electrolyte coating on said metal/metal salt coating, such that said immobilized electrolyte coating entirely covers said metal/metal salt coating,
  (4) an annealed perfluorocarbon copolymer coating on said immobilized electrolyte coating, such that said annealed perfluorocarbon copolymer coating entirely covers said immobilized electrolyte coating, and
  (5) a reference contact zone electrically connected to said second electrically conductive conductor, wherein said reference contact zone is utilized in making electrical contact between said second electrically conductive conductor and said pH sensing equipment;

(c) wherein said indicator and reference electrodes are electrically insulated from each other.

4. The solid state pH sensor of claim 3 having a single perfluorocarbon copolymer coating entirely covering both of said metal/metal oxide coating and said immobilized electrolyte coating.

5. The solid state pH sensor of claim 3 having a first barrier layer of a noble metal between said first electrically conductive conductor exposed portion and said metal/metal oxide coating, such that said first barrier layer entirely covers said first electrically conductive conductor exposed portion and said metal/metal oxide coating entirely covers said first barrier layer, and a second barrier layer of noble metal between said second electrically conductive conductor exposed portion and said metal/metal salt coating, such that said second barrier layer entirely covers said second electrically conductive conductor exposed portion and said metal/metal salt coating entirely covers said second barrier layer.

6. A solid state pH sensor for pH sensing equipment, said pH sensor comprising:

(a) an indicator electrode, said indicator electrode comprising
  (1) a first cermet conductor imbedded in a first portion of a ceramic substrate, said first cermet conductor having a first cermet conductor exposed portion,
  (2) a metal/metal oxide coating or a metal oxide coating on said first cermet conductor exposed portion, such that said metal/metal oxide or metal oxide coating entirely covers said first cermet conductor exposed portion,
  (3) an annealed perfluorocarbon copolymer coating on said metal/metal oxide or metal oxide coating, such that said perfluorocarbon entirely covers said metal/metal oxide or metal oxide coating, and (4) an indicator contact zone electrically connected to said first cermet conductor, wherein said indicator contact zone is utilized in making electrical contact between said first cermet conductor and said pH sensing equipment, and (b) a reference electrode, said reference electrode comprising (1) a second cermet conductor imbedded in a second portion of said ceramic substrate, said second cermet conductor having a second cermet conductor exposed portion, (2) a metal/metal salt coating on said second cermet conductor exposed portion, such that said metal/metal salt coating entirely covers said second cermet conductor exposed portion, (3) an immobilized electrolyte coating on said metal/metal salt coating, such that said immobilized electrolyte coating entirely covers said metal/metal salt coating, (4) an annealed perfluorocarbon copolymer coating on said immobilized electrolyte coating, such that said annealed perfluorocarbon copolymer coating entirely covers said immobilized electrolyte coating, and (5) a reference contact zone electrically connected to said second cermet conductor, wherein said reference contact zone is utilized in making electrical contact between said second cermet conductor and said pH sensing equipment;

(c) wherein said indicator and reference electrodes are electrically insulated from each other.

7. The solid state pH sensor of claim 6 having a single perfluorocarbon copolymer coating entirely covering both of said metal/metal oxide or metal oxide coating and said immobilized electrolyte coating.

8. The solid state pH sensor of claim 6, having a first barrier layer of a noble metal between said first cermet conductor exposed portion and said metal/metal oxide coating or said metal oxide coating, such that said first barrier layer entirely covers said first cermet conductor exposed portion and said metal/metal oxide coating or metal oxide coating entirely covers said first barrier layer, and a second barrier layer of noble metal between said second cermet conductor exposed portion and said metal/metal salt coating, such that said second barrier layer entirely covers said cermet conductor exposed portion and said metal/metal salt coating entirely covers said second barrier layer.

* * * * *